(12) United States Patent
Gupta et al.

(10) Patent No.: US 10,590,469 B2
(45) Date of Patent: Mar. 17, 2020

(54) METHODS FOR PERFORMING MULTIPLEXED REAL-TIME PCR IN A SELF-CONTAINED NUCLEIC ACID ANALYSIS POUCH

(71) Applicant: Roche Molecular Systems, Inc., Pleasanton, CA (US)

(72) Inventors: Amar Gupta, Danville, CA (US); Igor Kozlov, Danville, CA (US); Randall Saiki, Alameda, CA (US); Alison Tsan, Danville, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 2 days.

(21) Appl. No.: 16/141,515

(22) Filed: Sep. 25, 2018

(65) Prior Publication Data

US 2019/0024155 A1    Jan. 24, 2019

Related U.S. Application Data

(63) Continuation-in-part of application No. 15/705,821, filed on Sep. 15, 2017.

(60) Provisional application No. 62/435,595, filed on Dec. 16, 2016, provisional application No. 62/395,325, filed on Sep. 15, 2016.

(51) Int. Cl.
| | | |
|---|---|---|
| *C12Q 1/6837* | (2018.01) | |
| *C12Q 1/6806* | (2018.01) | |
| *C12Q 1/686* | (2018.01) | |
| *C12N 15/11* | (2006.01) | |
| *B01L 3/00* | (2006.01) | |
| *C12Q 1/6823* | (2018.01) | |
| *B01L 7/00* | (2006.01) | |

(52) U.S. Cl.
CPC ............ *C12Q 1/6837* (2013.01); *B01L 3/502* (2013.01); *B01L 7/52* (2013.01); *C12N 15/11* (2013.01); *C12Q 1/6806* (2013.01); *C12Q 1/686* (2013.01); *C12Q 1/6823* (2013.01); *B01L 2300/087* (2013.01); *B01L 2400/0481* (2013.01); *B01L 2400/0655* (2013.01); *B01L 2400/0683* (2013.01); *C12N 2310/321* (2013.01); *C12N 2310/3231* (2013.01); *C12N 2310/3517* (2013.01); *C12Q 2600/16* (2013.01); *C12Q 2600/166* (2013.01)

(58) Field of Classification Search
CPC .............. C12Q 2565/101; C12Q 1/686; C12Q 2561/113
See application file for complete search history.

(56) References Cited

U.S. PATENT DOCUMENTS

2004/0161788 A1*  8/2004  Chen ................... C12N 15/1003
                                                    435/6.11
2015/0148250 A1*  5/2015  Regan .................. C12Q 1/6848
                                                    506/9

* cited by examiner

*Primary Examiner* — Teresa E Strzelecka
(74) *Attorney, Agent, or Firm* — Charles M. Doyle

(57) ABSTRACT

The present invention describes methods for performing higher multiplexed real-time PCR for detection and quantitation of target nucleic acids using TAGS hydrolysis probes.

19 Claims, 23 Drawing Sheets

Specification includes a Sequence Listing.

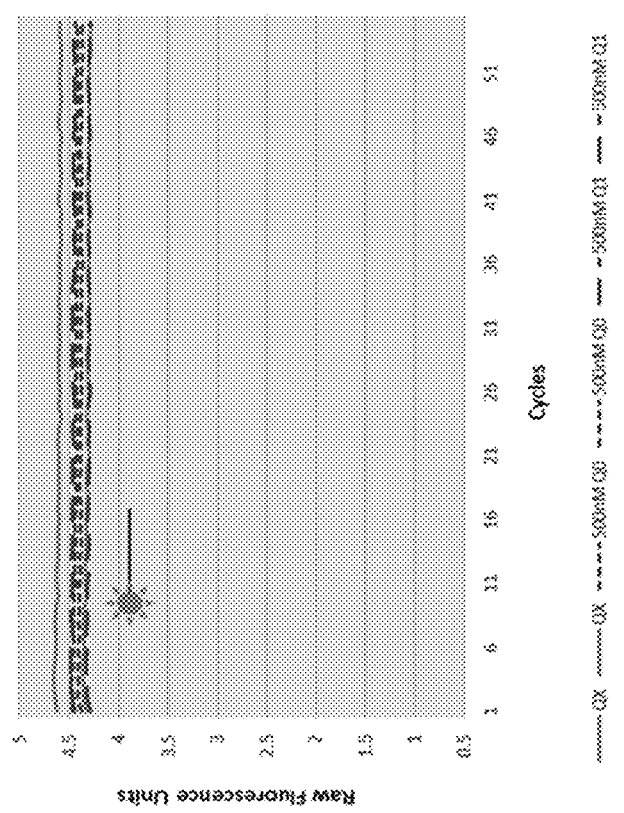
FIG. 6B
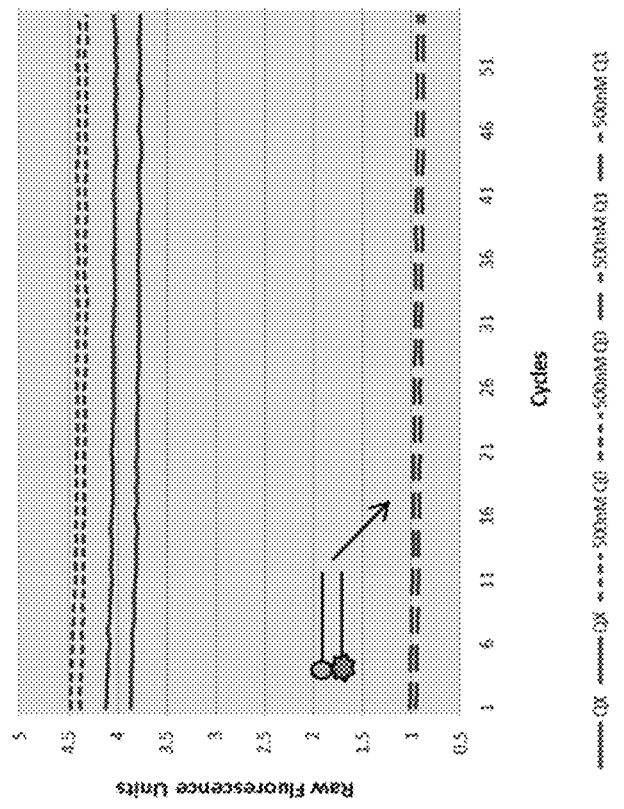
FIG. 6A
FIG. 6

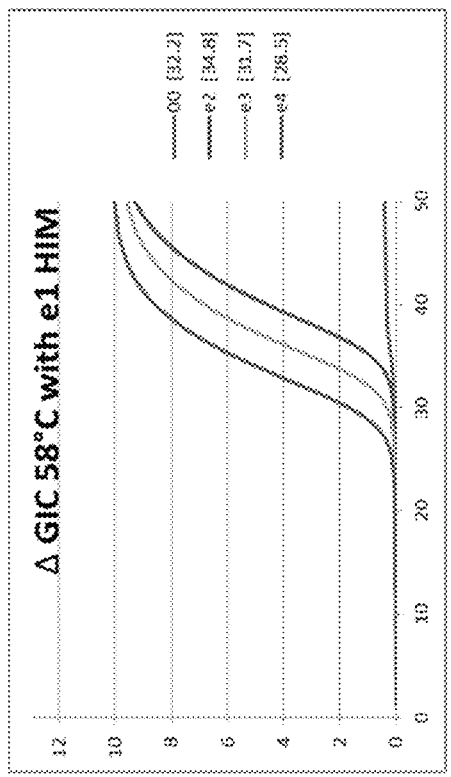
FIG. 7A
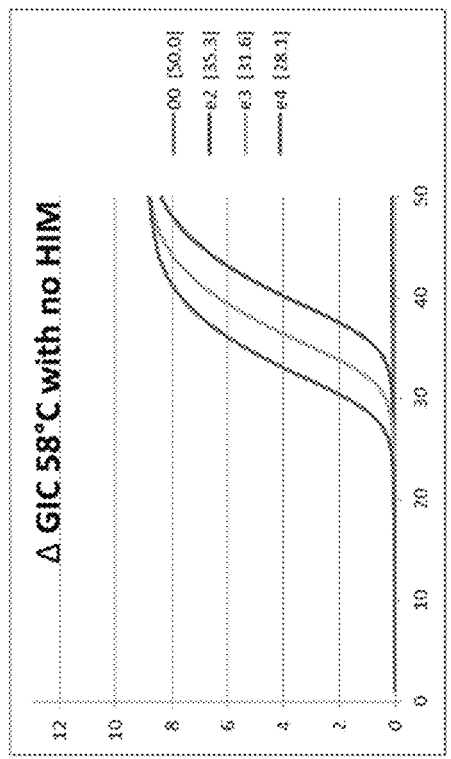
FIG. 7B
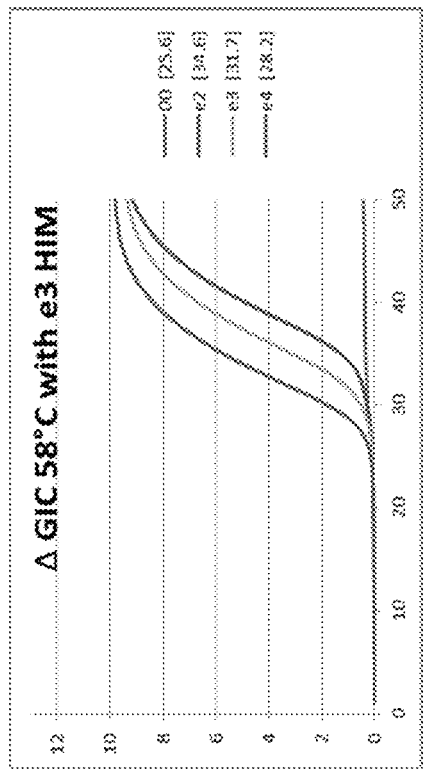
FIG. 7C
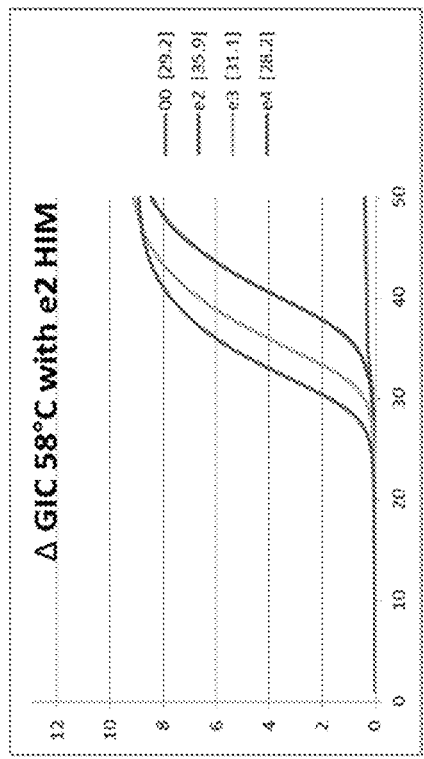
FIG. 7D
FIG. 7

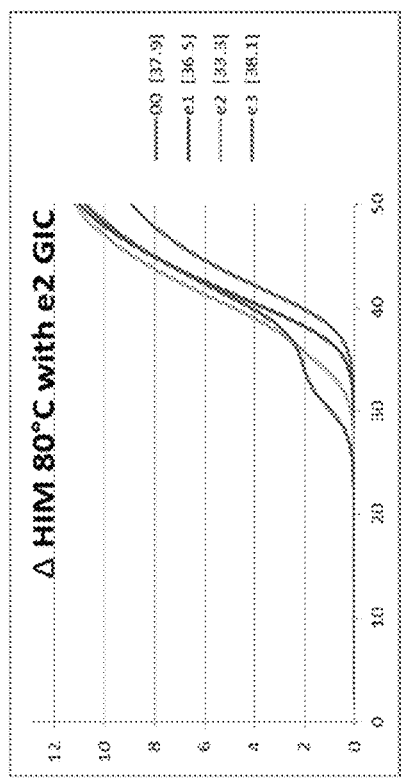
FIG. 8A
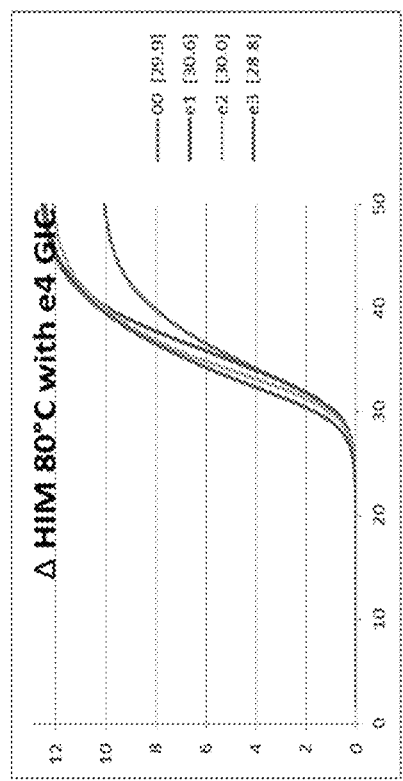
FIG. 8B
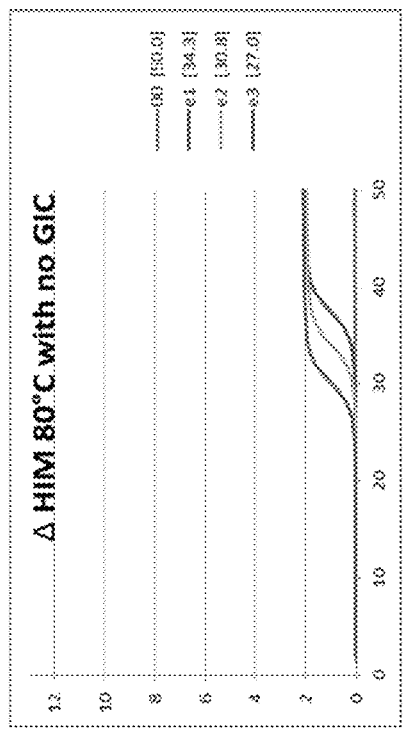
FIG. 8C
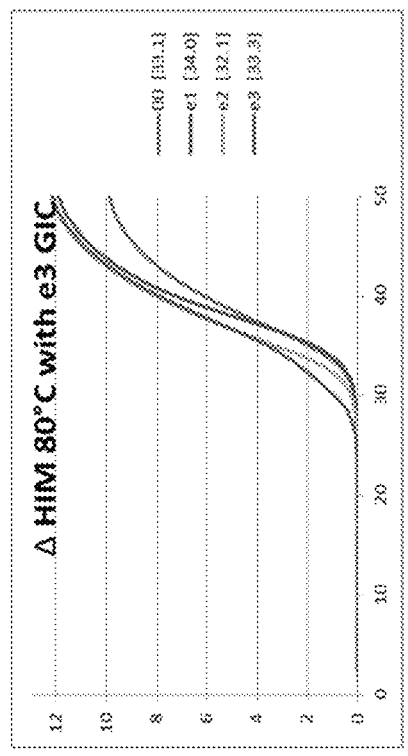
FIG. 8D
FIG. 8

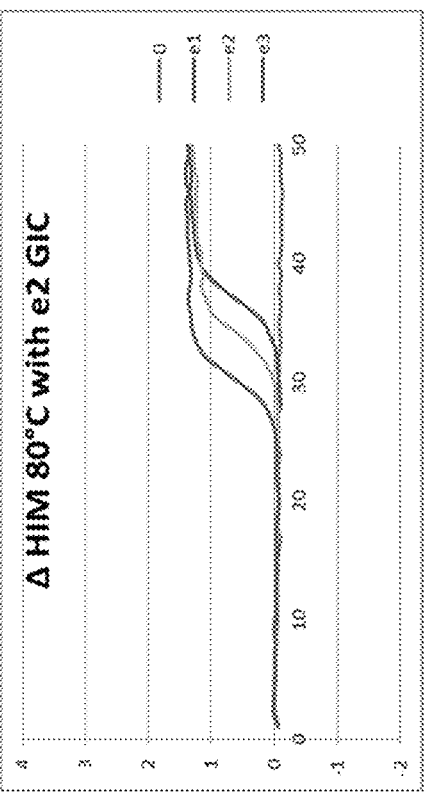
FIG. 9A
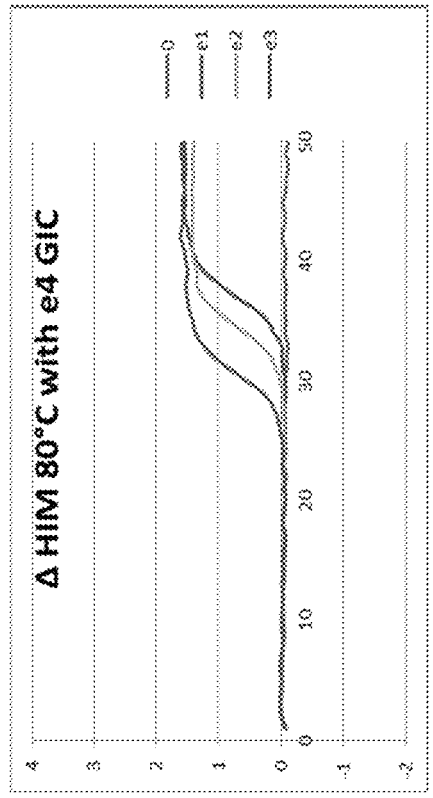
FIG. 9B
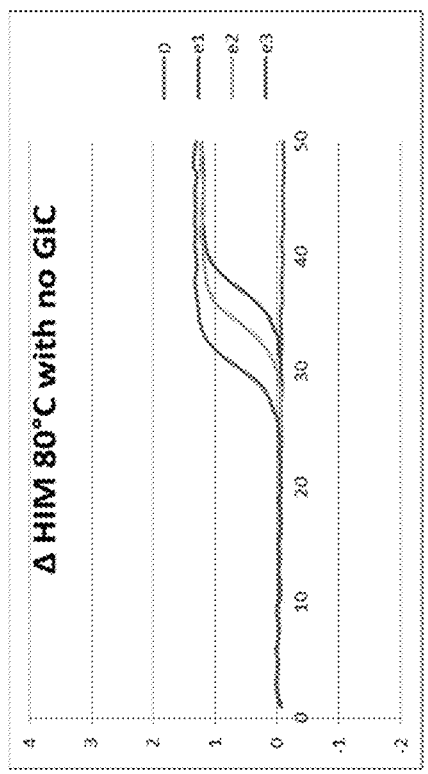
FIG. 9C
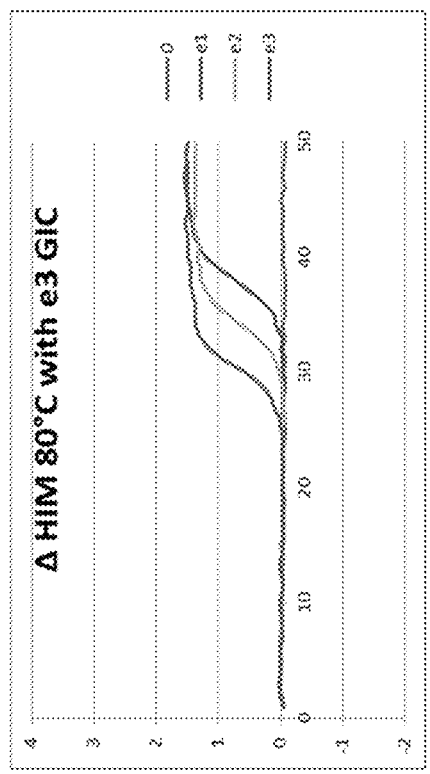
FIG. 9D
FIG. 9

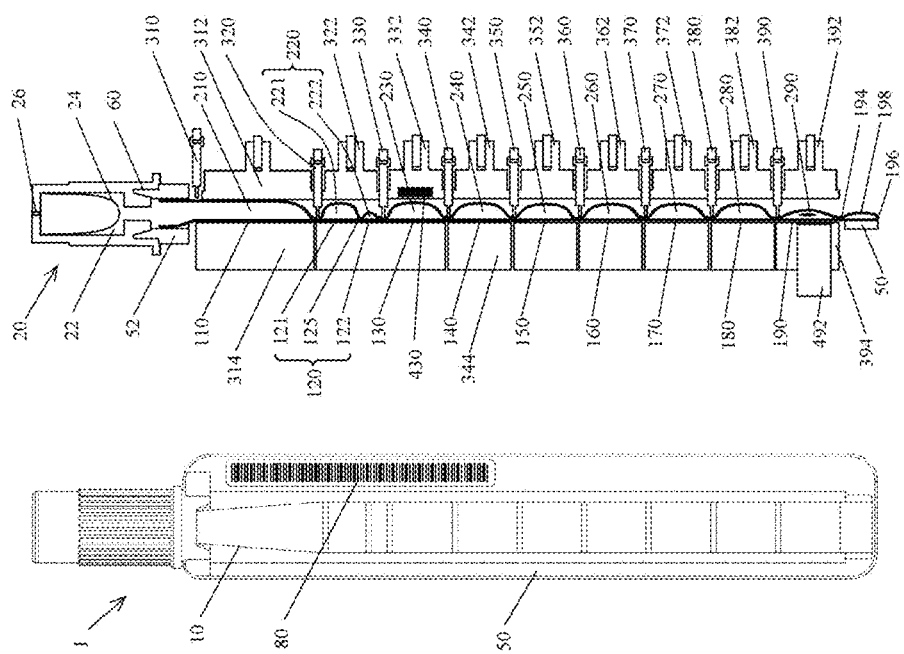

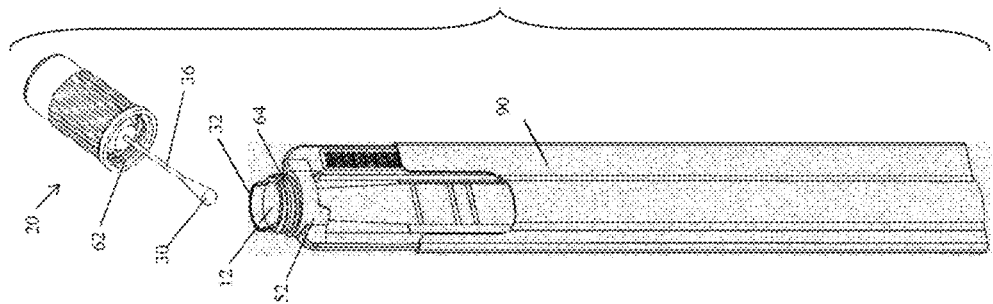
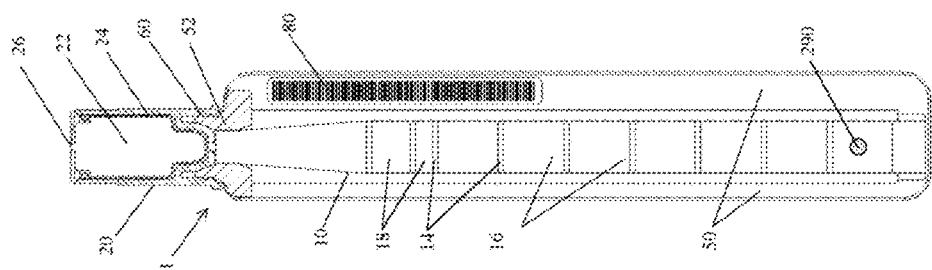
Fig. 14A
Fig. 14B

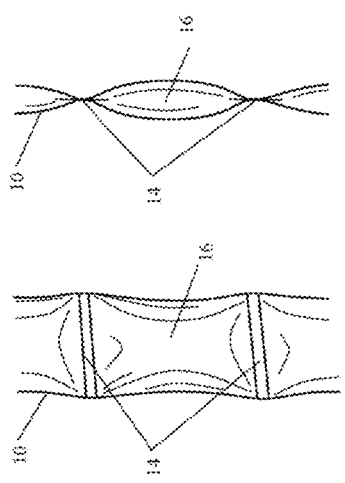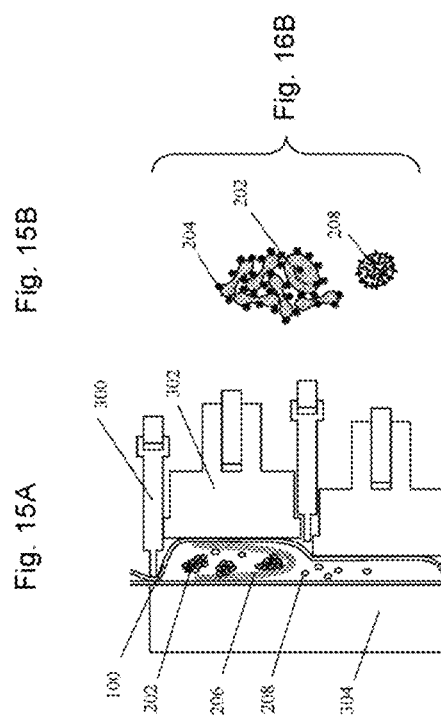

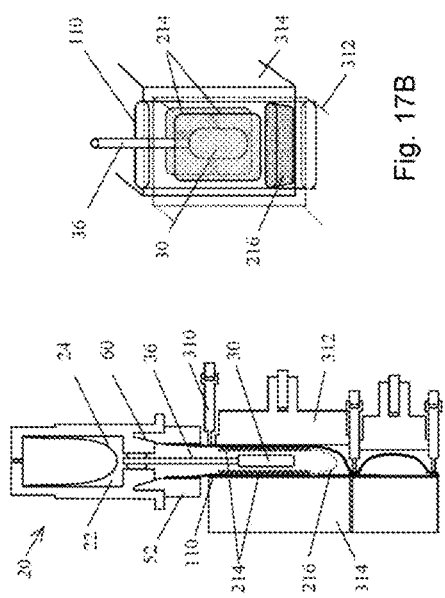
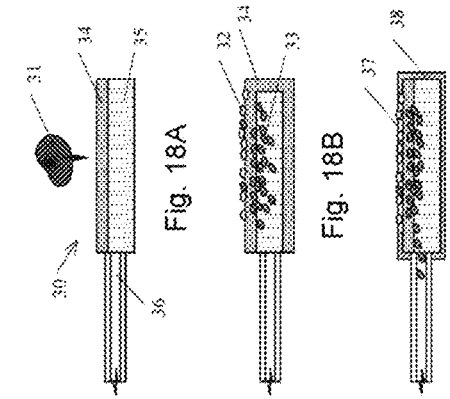
Fig. 17A
Fig. 17B
Fig. 18A
Fig. 18B
Fig. 18C

FIG. 22A
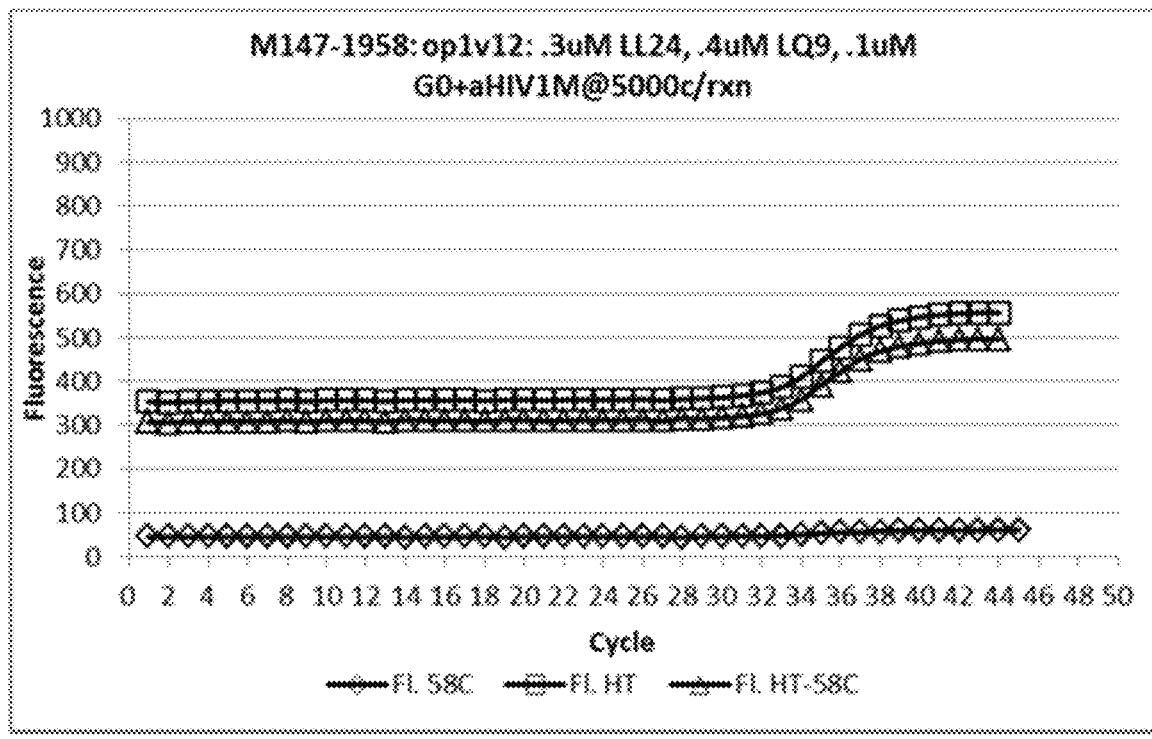
FIG. 22B
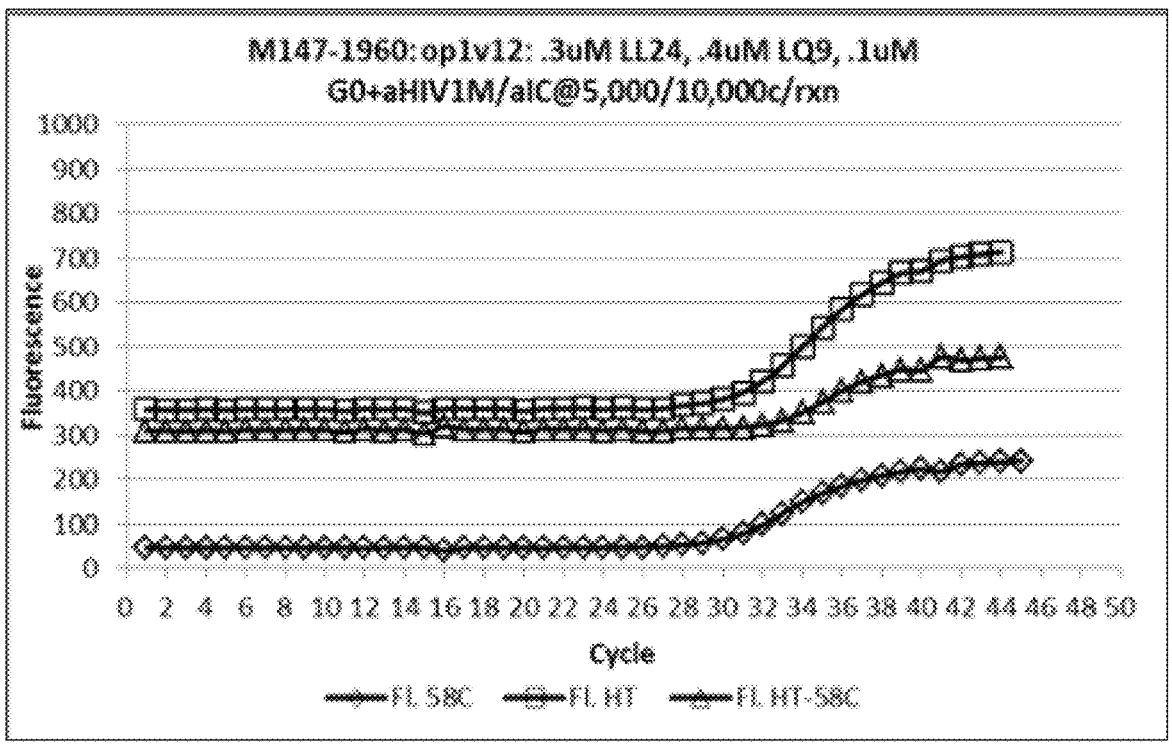
FIG. 22

FIG. 22C
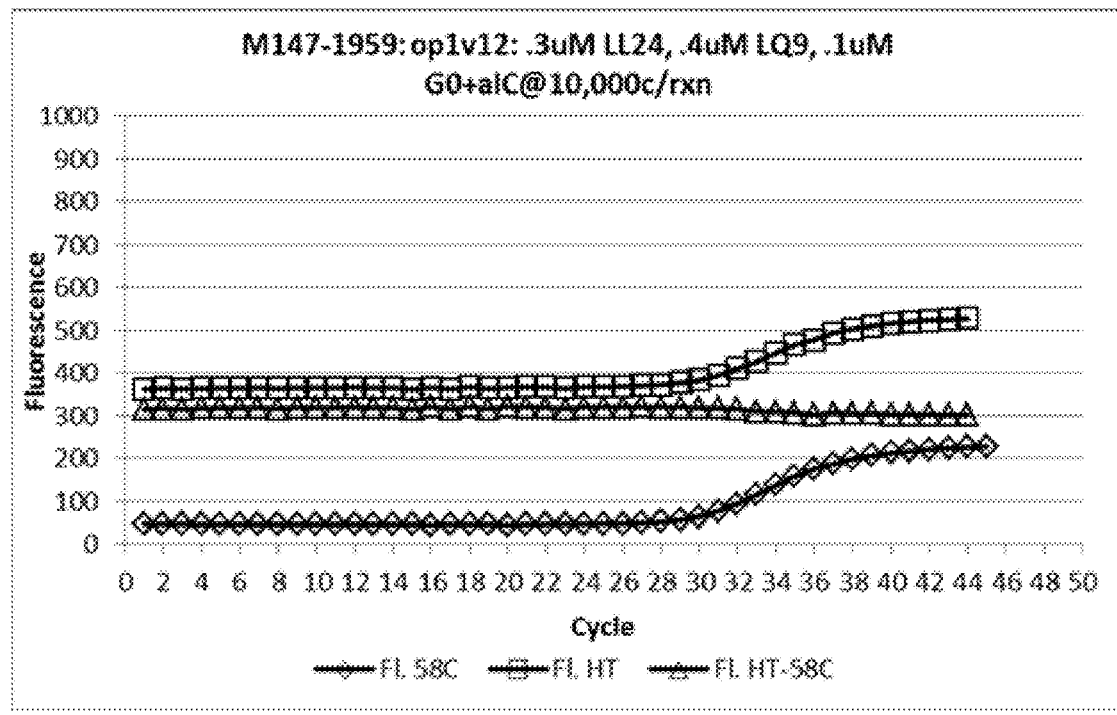
FIG. 22D
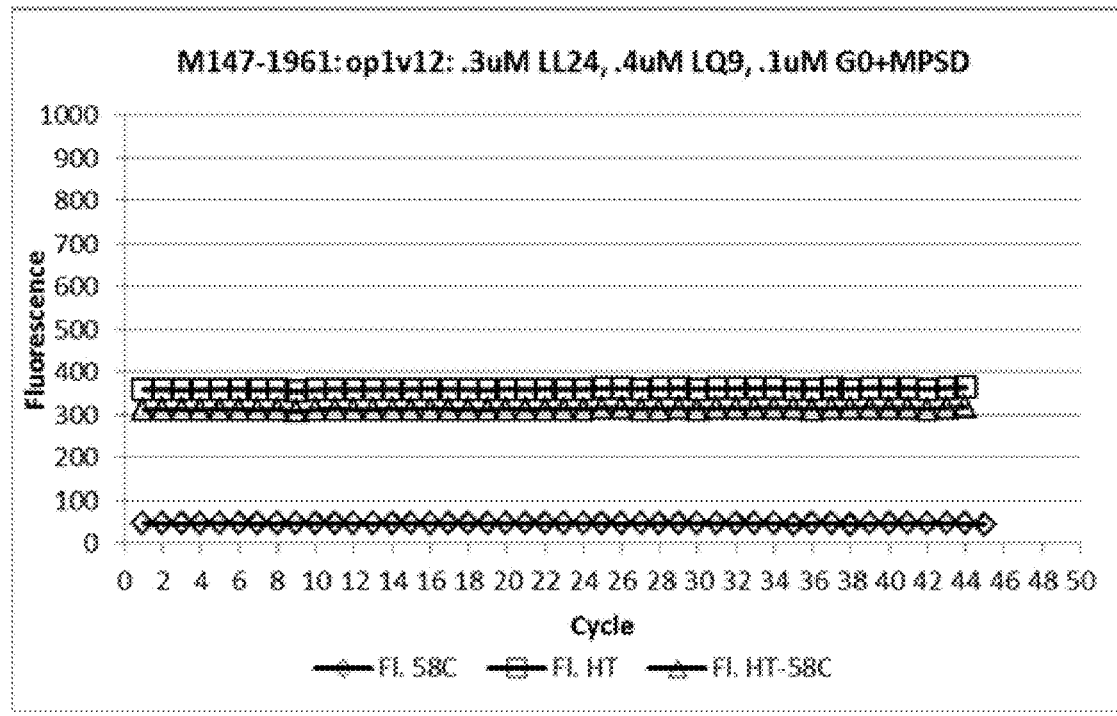
FIG. 22 (cont.)

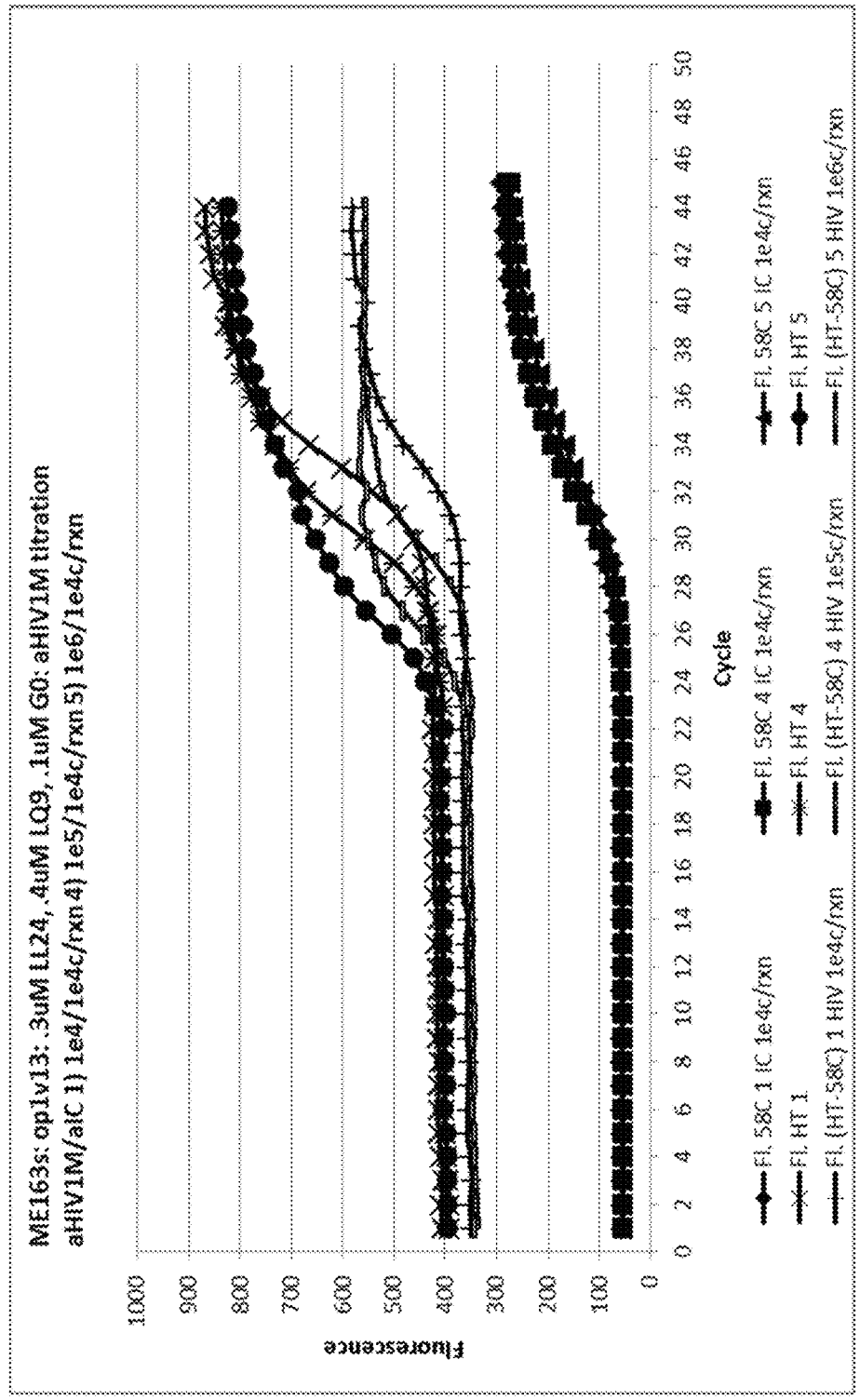

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
cgtcgccagt cagctccggt                                              20

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide

<400> SEQUENCE: 2
ccggagctga ctggcgacg                                               19

<210> SEQ ID NO 3
<211> LENGTH: 19
```

```
<212> TYPE: DNA
<213> ORGANISM: Artificial Sequence
<220> FEATURE:
<223> OTHER INFORMATION: Oligonucleotide

<400> SEQUENCE: 3
ccggagctga ctggcgacg                                              19

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide

<400> SEQUENCE: 4
tgcgcgtccc gttttgatac ttcgtaacgg tgc                              33

<210> SEQ ID NO 5
<211> LENGTH: 49
<212> TYPE: DNA
<213> ORGANISM: Artificial Sequence
<220> FEATURE:
<223> OTHER INFORMATION: Oligonucleotide

<400> SEQUENCE: 5
tctctagcag tggcgcccga acagggacca cacattggca ccgccgtct             49

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
agacggcggt gccaatgtgt g                                           21
```

METHODS FOR PERFORMING MULTIPLEXED REAL-TIME PCR IN A SELF-CONTAINED NUCLEIC ACID ANALYSIS POUCH

FIELD OF THE INVENTION

The present invention relates to methods for polymerase chain reaction (PCR), particularly to methods for performing multiplexed real-time PCR.

BACKGROUND OF THE INVENTION

The polymerase chain reaction (PCR) has become a ubiquitous tool of biomedical research, disease monitoring and diagnostics. Amplification of nucleic acid sequences by PCR is described in U.S. Pat. Nos. 4,683,195, 4,683,202, and 4,965,188. PCR is now well known in the art and has been described extensively in the scientific literature. See PCR Applications, ((1999) Innis et al., eds., Academic Press, San Diego), PCR Strategies, ((1995) Innis et al., eds., Academic Press, San Diego); PCR Protocols, ((1990) Innis et al., eds., Academic Press, San Diego), and PCR Technology, ((1989) Erlich, ed., Stockton Press, New York). A "real-time" PCR assay is able to simultaneously amplify and detect and/or quantify the starting amount of the target sequence. The basic TaqMan real-time PCR assay using the 5'-to-3' nuclease activity of the DNA polymerase is described in Holland et al., (1991) Proc. Natl. Acad. Sci. 88:7276-7280 and U.S. Pat. No. 5,210,015. A real-time PCR without the nuclease activity (a nuclease-free assay) has been described in U.S. Patent Publication No. 20100143901A1. The use of fluorescent probes in real-time PCR is described in U.S. Pat. No. 5,538,848.

A typical real-time PCR protocol with fluorescent probes involves the use of a labeled probe, specific for each target sequence. The probe is preferably labeled with one or more fluorescent moieties, which absorb and emit light at specific wavelengths. Upon hybridizing to the target sequence or its amplicon, the probe exhibits a detectable change in fluorescent emission as a result of probe hybridization or hydrolysis.

The major challenge of the real-lime assay however remains the ability to analyze numerous targets in a single tube. In virtually every field of medicine and diagnostics, the number of loci of interest increases rapidly. For example, multiple loci must be analyzed in forensic DNA profiling, pathogenic microorganism detection, multi-locus genetic disease screening and multi-gene expression studies, to name a few.

With the majority of current methods, the ability to multiplex an assay is limited by the detection instrument. Specifically, the use of multiple probes in the same reaction requires the use of distinct fluorescent labels. To simultaneously detect multiple probes, an instrument must be able to discriminate among the light signals emitted by each probe. The majority of current technologies on the market do not permit detection of more than four to seven separate wavelengths in the same reaction vessel. Therefore, using one uniquely-labeled probe per target, no more than four to seven separate targets can be detected in the same vessel. In practice, at least one target is usually a control nucleic acid. Accordingly, in practice, no more than three to six experimental targets can be detected in the same tube. The use of fluorescent dyes is also limited due to the spectral bandwidth where only about six or seven dyes can be fit within the visible spectrum without significant overlap interference. Thus the ability to multiplex an assay will not keep pace with the clinical needs, unless radical changes in the amplification and detection strategies are made.

An additional ability to multiplex a real-time amplification reaction is provided by a post-PCR melting assay. See U.S. Patent Publication No. 20070072211A1. In a melting assay, the amplified nucleic acid is identified by its unique melting profile. A melting assay involves determining the melting temperature (melting point) of a double-stranded target, or a duplex between the labeled probe and the target. As described in U.S. Pat. No. 5,871,908, to determine melting temperature using a fluorescently labeled probe, a duplex between the target nucleic acid and the probe is gradually heated (or cooled) in a controlled temperature program. The dissociation of the duplex changes the distance between interacting fluorophores or between fluorophore and quencher. The interacting fluorophores may be conjugated to separate probe molecules, as described in U.S. Pat. No. 6,174,670. Alternatively, one fluorophore may be conjugated to a probe, while the other fluorophore may be intercalated into a nucleic acid duplex, as described in U.S. Pat. No. 5,871,908. As yet another alternative, the fluorophores may be conjugated to a single probe oligonucleotide. Upon the melting of the duplex, the fluorescence is quenched as the fluorophore and the quencher are brought together in the now single-stranded probe.

The melting of the nucleic acid duplex is monitored by measuring the associated change in fluorescence. The change in fluorescence may be represented on a graph referred to as "melting profile." Because different probe-target duplexes may be designed to melt (or reanneal) at different temperatures, each probe will generate a unique melting profile. Properly designed probes would have melting temperatures that are clearly distinguishable from those of the other probes in the same assay. Many existing software tools enable one to design probes for a same-tube multiplex assay with these goals in mind. For example, Visual OMP™ software (DNA Software, Inc., Ann Arbor, Mich.) enables one to determine melting temperatures of nucleic acid duplexes under various reaction conditions.

The method of multiplex PCR using fluorescence detection and a subsequent post-amplification melting assay is described in U.S. Pat. No. 6,472,156. The number of targets detectable by such a method is a product of the number of detectable wavelengths and the number of distinguishable melting profiles. Therefore adding a melting assay to color detection was a step forward in the ability to detect multiple targets.

The post-amplification melting assay is most commonly used for qualitative purposes, i.e. to identify target nucleic acids, see U.S. Pat. Nos. 6,174,670; 6,427,156; and 5,871,908. It is known to obtain a melting peak by differentiating the melting curve function. Ririe et al. ("Product differentiation by analysis of DNA melting curves during the polymerase chain reaction," (1997) Anal. Biochem. 245: 154-160) observed that differentiation helps resolve melting curves generated by mixtures of products. After differentiation, the melting peaks generated by each component of the mixture become easily distinguishable. It was also previously known that the post-amplification melting signal, i.e. melting peak, is higher in proportion to the amount of the nucleic acid in the sample. For example, U.S. Pat. No. 6,245,514 teaches a post-amplification melt assay using a duplex-intercalating dye, to generate a derivative melting peak, and then, using proprietary software, to integrate the peak. The integration provides information about the efficiency of amplification and relative amount of the amplified nucleic add.

In practice, it would be desirable to move beyond a qualitative assay and be able to quantify multiple targets in the same sample. See e.g. Sparano et al. "Development of the 21-gene assay and its application in clinical practice and clinical trials," J. Clin. Oncol. (2008) 26(5):721-728. The ability to quantify the amount of target is useful in clinical applications, such as determination of viral load in a patient's serum, measuring the level of expression of a gene in response to drug therapy, or determining the molecular signature of a tumor to predict its response to therapy.

In a real-time PCR assay, the signal generated by the labeled probe can be used to estimate the amount of input target nucleic acid. The greater the input, the earlier the fluorescence signal crosses a predetermined threshold value (Ct). Therefore one can determine relative or absolute amounts of the target nucleic acid by comparing the samples to each other or to a control sample with known amount of nucleic acid. However, the existing methods are limited in their ability to simultaneously quantify multiple targets. As with the qualitative detection of multiple targets, the limiting factor is the availability of spectrally-resolvable fluorophores. As explained above, state-of-the-art fluorescent label technology is not able to obtain distinct signals from more than six or seven separate fluorescently labeled probes in the same tube. Therefore a radically different experimental approach is needed to permit amplification and detection of numerous nucleic acid targets during real-time PCR.

Many methods for detection of target nucleic acids are known. Currently available homogeneous assays for nucleic acid detection include the TaqMan®, Ampliflour®, dye-binding, allele-selective kinetic PCR and Scorpions primer assays. These assay procedures are not readily multiplexed due to the requirement for a different dye for each target nucleic acid to be detected, and thus are limited in their potential for improvement. To overcome such limitations, several recent studies have disclosed the use of oligonucleotide probes containing a cleavable "tag" portion which can be readily separated and detected (e.g. see Chenna et al, U.S. Patent Publication No. 2005/0053939A1 and U.S. Pat. No. 8,133,701). More recently, improved methods to perform multiplexed nucleic acid target identification by using structure-based oligonucleotide probe cleavage have been described in U.S. Patent Publication Nos. 2014/0272955, U.S. 2015/0176075, and U.S. 2015/0376681. Further methods to detect target nucleic acid sequence from DNA or a mixture of nucleic acid by the use of a combination of "Probing and Tagging Oligonucleotide" (PTO) and "Capturing and Templating Oligonucleotide" (CTO) in a so-called PTO Cleavage and Extension assay have been described in U.S. Pat. No. 8,809,239. However the need still exists for an accurate method to perform high-throughput multiplex detection of target nucleic acids.

SUMMARY OF THE INVENTION

The present invention provides'for novel methods for nucleic acid sequence detection, particularly detection of multiple target nucleic acids using a real-time PCR assay. The methods are performed by the use of novel oligonucleotide probes having two unique features, a non-complementary tag portion and a quenching molecule. The methods may be performed using a device for processing a sample that includes a processing unit e.g., an analyzer, having an opening to receive a sample vessel and at least one processing station positioned along the opening. The processing unit includes at least one compression member adapted to compress the sample vessel within the opening and thereby displace a content of the sample vessel within the sample vessel. The energy transfer element may transfer thermal energy to or from the content within the sample vessel. The sample vessel may comprise a sample introduction port adapted to receive a sample aliquot; an internal control compartment comprising a composition as described herein; and a PCR analysis region comprising one or more additional compartments each configured to conduct one or more steps of a PCR analysis, e.g., reagent preparation, target enrichment, inhibitor removal, nucleic acid extraction, amplification, and/or real-time detection.

Therefore in one aspect, the invention provides fora method for detecting a target nucleic acid in a sample, comprising (a) contacting a sample suspected of containing said target nucleic acid in a reaction vessel with a mixture comprising (i) at least one pair of oligonucleotide primers, each oligonucleotide primer of the pair being capable of hybridizing to opposing strands of a subsequence of the target nucleic acid; (ii) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of the target nucleic acid that is bounded by the pair of oligonucleotide primers, the probe further comprising an interactive dual label comprising a reporter moiety located on the tag portion and a first quencher moiety located on the annealing portion, and wherein the reporter moiety is separated from the first quencher moiety by a nuclease susceptible cleavage site; and wherein the tag portion hybridizes to a quenching oligonucleotide that comprises one or more quencher moieties capable of quenching the reporter moiety when the quenching, oligonucleotide is hybridized to the tag portion; (b) wherein the reaction vessel is a tubule, comprising (i) a proximal end having an opening through which a sample is introducible; (ii) a distal end; and (iii) at least a first segment containing at least one nucleic acid extraction reagent, a second segment distal to the first segment and containing awash reagent, and a third segment distal to the second segment and containing one or more amplification reagents, each of the segments being (A) defined by the tubule; (B) fluidly isolated, at least in part, by a fluid-tight seal formed by a bonding of opposed wall portions of the tubule to one another such that (1) the seal is broken by application of fluid pressure on a segment that is fluidly isolated in part by the seal; and (2) the seal is capable of being clamped where the opposed wall portions of the tubule are bonded, without breaking the seal, to prevent the seal from being broken by application of fluid pressure on a segment that is fluidly isolated in part by the seal; (C) so expandable as to receive a volume of fluid expelled from another segment; and so compressible as to contain substantially no fluid when so compressed; (iv) a cap for dosing the opening, the cap containing a chamber in fluid communication with the tubule, and the cap permitting free escape of gasses but retaining all liquid volumes and infectious agents in the tube; (v) a rigid frame to which the tubule's proximal and distal ends are held; and (vi) an integral tubule tensioning mechanism or an attachment of the tubule to the frame that pulls the tubule sufficiently taut so as to facilitate compression and flattening of the tubule; (c) amplifying the target nucleic acid in the reaction vessel containing the mixture by PCR using a nucleic acid polymerase having 5' to 3' nuclease activity such that during an extension step of each PCR cycle, the nuclease activity of the nucleic acid polymerase allows cleavage and separation of the tag portion from the first quencher moiety on the annealing portion of the probe, the PCR being performed by cycling the mixture between two adjacent segments, held at different temperatures, of the reaction vessel; (d) measuring a temperature-corrected signal from the reporter moiety on the oligonucleotide probe in the mixture while in One of the two adjacent segments, the mixture being at a first temperature at which the quenching oligonucleotide is bound to the tag portion; (c) after a predetermined time interval, measuring a suppressed signal from the reporter moiety on the oligonucleotide probe in the mixture while in the one of the two adjacent segments, the mixture being at a second temperature within the same of the one of the two adjacent segments at which the quenching oligonucleotide is bound to the tag portion; (f) obtaining a calculated signal value by subtracting the suppressed signal detected at the second temperature from the temperature-corrected signal detected at the first temperature; (g) repeating steps (c) through (g) through multiple PCR cycles; and (h) measuring the calculated signal values from the multiple PCR cycles to detect the presence of the target nucleic acid.

In one embodiment, the tag portion comprises a modification such that it is not capable of being extended by a nucleic acid polymerase. In one embodiment, the reporter moiety is on the tag portion of the oligonucleotide probe. In another embodiment, the reporter moiety is located on the annealing portion of the oligonucleotide probe and is able to interact in a temperature-dependent manner with the quenching molecule that comprises the second quencher moiety. In one embodiment, the tag portion comprises a nucleotide sequence non-complementary to the target nucleic acid sequence and the quenching molecule is an oligonucleotide comprising a nucleotide sequence at least partially complementary to the tag portion of the oligonucleotide probe and binds to the tag portion by hybridization. In another embodiment, the tag portion of the oligonucleotide probe or the quenching molecule or both the tag portion and the quenching molecule contain one or more nucleotide modifications. In yet another embodiment, the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations thereof.

In one embodiment, the reporter moiety is a fluorescent dye and the quencher moiety quenches a detectable signal from the fluorescent dye.

In another aspect, the present invention provides a novel reaction vessel, comprising (a) a proximal end having an opening through which a sample is introducible; (b) a distal end; and (c) at least a first segment: containing at least one nucleic acid extraction reagent, a second segment distal to the first segment and containing a wash reagent, and a third segment distal to the second segment and containing one or more amplification reagents, each of the segments being (i) defined by the tubule; (ii) fluidly isolated, at least in part, by a fluid-tight seal formed by a bonding of opposed wall portions of the tubule to one another such that (A) the seal is broken by application of fluid pressure on a segment that is fluidly isolated in part by the seal; and (B) the seal is capable of being clamped where the opposed wall portions of the tubule are bonded, without breaking the seal, to prevent the seal from being broken by application of fluid pressure on a segment that is fluidly isolated in part by the seal; (iii) so expandable as to receive a volume of fluid expelled from another segment; and so compressible as to contain substantially no fluid when so compressed; (d) a cap for closing the opening, the cap containing a chamber in fluid communication with the tubule, and the cap permitting free escape of gasses but retaining all liquid volumes and infectious agents in the tube; (e) a rigid frame to which the tubule's proximal and distal ends are held; and (f) an integral tubule tensioning mechanism or an attachment of the tubule to the frame that pulls the tubule sufficiently taut so as to facilitate compression and flattening of the tubule; (g) the reaction vessel containing (i) at least one pair of oligonucleotide primers, each oligonucleotide primer of the pair being capable of hybridizing to opposing strands of a subsequence of the target nucleic acid; (ii) an oligonucleotide probe, comprising a tag portion and an annealing portion on the same strand, wherein the tag portion comprises a nucleotide sequence non-complementary to the target nucleic acid sequence, and the annealing portion comprises, a nucleotide sequence at least partially complementary to the target nucleic acid sequence and which hybridizes to a region of the target nucleic acid that is bounded by the pair of oligonucleotide primers, the probe further comprising an interactive dual label comprising a reporter moiety located on the tag portion and a first quencher moiety located on the annealing portion, and wherein the reporter moiety is separated from the first quencher moiety by a nuclease susceptible cleavage site; and wherein the tag portion hybridizes to a quenching oligonucleotide that comprises one or more quencher moieties capable of quenching the reporter moiety when the quenching oligonucleotide is hybridized to the tag portion.

In another aspect, the present invention provides a sample processing apparatus, comprising (a) a processing unit having an opening to receive a sample vessel containing a sample, the processing unit having a first processing station, a second processing station, and a third processing station positional along the opening, (b) the first processing station including a first compression member adapted to compress the sample vessel within the opening and a first energy transfer element for transferring energy to the sample at the first processing station, (c) the second processing station including a second compression member adapted to compress the sample vessel within the opening and a second energy transfer element for transferring energy to the sample at the second processing station, and (d) the third processing station including a third compression member adapted to compress the sample vessel within the opening and a third energy transfer element for transferring energy to the sample at the third processing station, wherein compression of the sample vessel by one of the compression members displaces the sample within the sample vessel between the processing stations; and (e) a reaction vessel insertable in the opening and comprising (i) a proximal end having an opening through which a sample is introducible; (ii) a distal end; and (iii) at least a first segment containing at least one nucleic acid extraction reagent, a second segment distal to the first segment and containing a wash reagent, and a third segment distal to the second segment and containing one or more amplification reagents, each of the segments being (A) defined by the tubule; (B) fluidly isolated, at least in part, by a fluid-tight seal formed by a bonding of opposed wall portions of the tubule to one another such that (a) the seal is broken by application of fluid pressure on a segment that is fluidly isolated in part by the seal; and (b) the seal is capable of being clamped where the opposed wall portions of the tubule are bonded, without breaking the seal, to prevent the seal from being broken by application of fluid pressure on a segment that is fluidly isolated in part by the seal; (C) so expandable as to receive a volume of fluid expelled from another segment; and so compressible as to contain substantially no fluid when so compressed; (iv) a cap for closing the opening, the cap containing a chamber in fluid communication with the tubule, and the cap permitting free escape of gasses but retaining all liquid volumes and infectious agents in the tube; (v) a rigid frame to which the tubule's proximal and distal ends are held; and (vi) an integral tubule tensioning mechanism or an attachment of the tubule to the frame that pulls the tubule sufficiently taut so as to facilitate compression and flattening of the tubule; (vii) one of the segments containing (A)at least one pair of oligonucleotide primers, each oligonucleotide primer of the pair being capable of hybridizing to opposing strands of a subsequence of the target nucleic acid; (B) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of the target nucleic acid that is bounded by the pair of oligonucleotide primers, the probe further comprising an interactive dual label comprising a reporter moiety located on the tag portion and a first quencher moiety located on the annealing portion, and wherein the reporter moiety is separated from the first quencher moiety by a nuclease susceptible cleavage site; and wherein the tag portion hybridizes to a quenching oligonucleotide that comprises one or more quencher moieties capable of quenching the reporter moiety when the quenching oligonucleotide is hybridized to the tag portion.

In one embodiment, the first tag portion is attached to the 3' terminus of the first annealing portion of the first oligonucleotide probe and the second tag portion is attached to the 3' terminus of the second annealing portion of the second oligonucleotide probe. In another embodiment, the first tag portion is attached to the 3' terminus of the first annealing portion of the first oligonucleotide probe and the second tag portion is attached to the 5' terminus of the second annealing portion of the second oligonucleotide probe. In another embodiment, the first tag portion is attached to the 3' terminus of the first annealing portion of the first oligonucleotide probe and the second tag portion is attached via a linker to a region of the second annealing portion of the second oligonucleotide probe.

In one embodiment, the first tag portion is attached to the 5' terminus of the first annealing portion of the first oligonucleotide probe and the second tag portion is attached to the 5' terminus of the second annealing portion of the second oligonucleotide probe. In another embodiment, the first tag portion is attached to the 5' terminus of the first annealing portion of the first oligonucleotide probe and the second tag portion is attached to the 3' terminus of the second annealing portion of the second oligonucleotide probe. In another embodiment, the first tag portion is attached to the 5' terminus of the first annealing portion of the first oligonucleotide probe and the second tag portion is attached via a linker to a region of the second annealing portion of the second oligonucleotide probe.

In one embodiment, the first tag portion is attached via a linker to a region of the first annealing portion of the first oligonucleotide probe and the second tag portion is attached to the 5' terminus of the second annealing portion of the second oligonucleotide probe. In another embodiment, the first tag portion is attached via a linker to a region of the first annealing portion of the first oligonucleotide probe and the second tag portion is attached to the 3' terminus of the second annealing portion of the second oligonucleotide probe. In another embodiment, the first tag portion is attached via a linker to a region of the first annealing portion of the first oligonucleotide probe and the second tag portion is attached via a linker to a region of the second annealing portion of the second oligonucleotide probe.

In yet another aspect, the invention provides for a kit for detecting two or more target nucleic acid sequences in a sample comprising a segmented flexible tubule comprising (a) at least one pair of oligonucleotide primers, each oligonucleotide primer of the pair being capable of hybridizing to opposing strands of a subsequence of the target nucleic acid; (b) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of the target nucleic acid that is bounded by the pair of oligonucleotide primers, the probe further comprising an interactive dual label comprising a reporter moiety located on the tag portion and a first quencher moiety located on the annealing portion, and wherein the reporter moiety is separated from the first quencher moiety by a nuclease susceptible cleavage site; and wherein the tag portion hybridizes to a quenching oligonucleotide that comprises one or more quencher moieties capable of quenching the reporter moiety when the quenching oligonucleotide is hybridized to the tag portion; and (c) at least one quenching oligonucleotide comprising a nucleotide sequence at least partially complementary to the tag portion of the oligonucleotide probe and hybridizes to the tag portion to form a duplex, wherein the quenching oligonucleotide comprises a second quencher moiety which quenches the detectable signal generated by the fluorescent moiety on the tag portion when the quenching oligonucleotide is hybridized to the tag portion.

BRIEF DESCRIPTION OF THE DRAWINGS

FIG. 6 shows the results of the hybridization and dissociation at two temperatures using a quenching oligonucleotide and a fluorescently labeled complementary oligonucleotide as described in Example 1. FIG. 6A: 58° C.; FIG. 6B: 80° C.

FIG. 7 shows the PCR growth curves generated from an internal control template (GIC) at 0 ("00"), 100 ("e2"), 1,000 ("e3") or 10,000 ("e4") copies ("cp")/rxn using a standard TaqMan® probe G0 and FAM fluorescence readings at 58° C. and in the absence of HIV-1 Group M template (HIM) (FIG. 7A) or in the presence of HIM at 10 ("e1") cp/rxn (FIG. 7B), 100 ("e2") cp/rxn (FIG. 7C) and 1,000 ("e3") cp/rxn (FIG. 7D).

FIG. 8 shows the PCR growth curves generated from HIM at 0 ("00"), 10("e1"), 100 ("e2") or 1,000 ("e3") copies ("cp")/rxn using a TAGS probe (L24) with a complementary quenching oligonucleotide (Q9) and FAM fluorescence readings at 80° C. and in the absence of GIC (FIG. 8A) or in the presence of GIC at 100 ("e2") cp/rxn (FIG. 8B), 1,000 ("e3") cp/rxn (FIG. 8C) and 10,000 ("e4") cp/rxn (FIG. 8D).

FIG. 9 shows the derived growth curves from HIM at 0 ("0"), 10("e1"), 100 ("e2") or 1,000 ("e3") copies ("cp")/rxn generated by having 84% of the 58° C. fluorescence signals subtracted from the 80° C. fluorescence signals in the absence of GIC (FIG. 9A) or in the presence of GIC at 100 ("e2") cp/rxn (FIG. 9B), 1,000 ("e3") cp/rxn (FIG. 9C) and 10,000 ("e4") cp/rxn (FIG. 9D).

FIG. 13A is a front elevation view of an exemplary embodiment of a sample tube including a tubule. FIG. 13B is a cross sectional view of a sample tube positioned inside an analyzer.

FIG. 14A is a cross sectional view of a sample tube including a tubule. FIG. 14B is a perspective view of another exemplary embodiment of a sample tube.

FIGS. 15A-B are, respectively, front and side elevation views of an exemplary embodiment of a sample tubule.

FIG. 16A is across sectional view of an exemplary embodiment of a sample tube positioned in an analyzer. FIG. 16B is a schematic dose-up view of an embodiment of a biological sample.

FIGS. 17A-B are, respectively, cross sectional and perspective views of exemplary embodiments of sample tubes positioned in analyzers.

FIGS. 18A-C are cross sectional views of an embodiment of a sample collection device receiving a sample.

FIG. 22 shows the PCR growth curves generated from the experiment described in Example 7, where an internal control template (GIC), and an HIV-1 Group M template (HIM) can be individually or simultaneously detected in the FAM channel using a Taqman probe and a TAGS probe. FIG. 22A: 5000 copies HIM target only; FIG. 22B: 5000 copies HIM+10000 copies GIC targets; FIG. 22C: 10,000 copies GIC only; FIG. 22D: buffer only.

FIG. 23B shows an overlay of growth curves from reactions with $10^4$ copies of GIC, and $10^4$, $10^5$, or $10^6$ copies of HIM targets.

DETAILED DESCRIPTION OF THE INVENTION

Definitions

Figure 1:
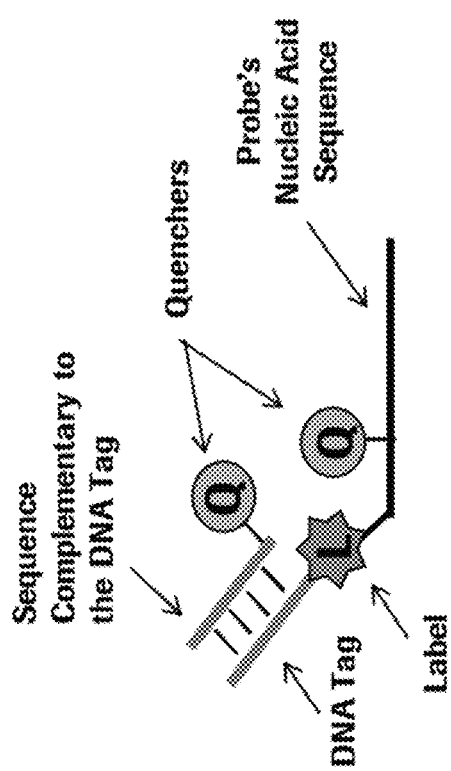
FIG. 1 is a graphical description of one embodiment of the oligonucleotide probe (TAGS probe) used to perform the methods of the invention. Q=quencher, L=label.

The term "sample" as used herein includes any specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "target" or "target nucleic acid" as used herein are intended to mean any molecule whose presence is to be detected or measured or whose function, interactions or properties are to be studied. Therefore, a target includes essentially any molecule for which a detectable probe (e.g., oligonucleotide probe) or assay exists, or can be produced by one skilled in the art. For example, a target may be a biomolecule, such as a nucleic acid molecule; a polypeptide, a lipid, or a carbohydrate, which is capable of binding with or otherwise coming in contact with a detectable probe (e.g., an antibody), wherein the detectable probe also comprises nucleic acids capable of being detected by methods of the invention. As used herein, "detectable probe" refers to any molecule or agent capable of hybridizing or annealing to a target biomolecule of interest and allows for the specific detection of the target biomolecule as described herein. In one aspect of the invention, the target is a nucleic acid, and the detectable probe is an oligonucleotide. The terms "nucleic acid" and "nucleic acid molecule" may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/nonnaturally-occurring, nucleotides, including nucleoside tri, di, and monophosphates as well as monophosphate monomers present within polynucleic acid or oligonucleotide. A nucleotide may also be a ribonucleotide; 2'-deoxynucleotide; or 2',3'-deoxynucleotide as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi- and/or psi-linker-modified; mass label-modified; phosphodiester modifications or replacements including phosphorothioate, methylphosphonate, boranophosphate, amide, ester, ether; and/or a basic or complete internucleotide replacements, including cleavage linkages such a photocleavable nitrophenyl moieties.

The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have either a known or unknown sequence or structure.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs, as noted above. Where an enzyme has specific oligonucleotide or polynucleotide substrate requirements for activity, e.g., single stranded DNA, RNA/DNA duplex, or the like, then selection of the appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a target nucleic acid template and facilitates the detection of an oligonucleotide probe. In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. Primers can be of a variety of lengths and are often less than 50 nucleotides in length, for example 12-25 nucleotides, in length. The length and sequences of primers for use in PCR can be deSigned based on principles known to those of skill in the art.

The term " oligonucleotide probe" as used herein refers to a polynucleotide sequence capable of hybridizing or annealing to a target nucleic acid of interest and allows for the specific detection of the target nucleic acid A "reporter moiety" or "reporter molecule" is a molecule that confers a detectable signal. The detectable phenotype can be colorimetric, fluorescent or luminescent, for example. Examples of fluorescent reporter moieties include, e.g., fluorescein (FAM), hexacholorofluorescein (HEX), JA270 (Roche Molecular Systems), cyanine dyes (e.g., CY3.5, CY5 or CY5.5).

A "quencher moiety" or "quencher molecule" is a molecule that is able to quench the detectable signal from the reporter moiety. Examples of quencher moieties used with fluorescent reporters include, e.g., the so-called dark quenchers, such as Black Hole Quenchers (BHQ-1 or BHQ-2) (LCC BioSearch Technologies) or Iowa Black (Integrated DNA Technologies); and fluorescent moities that use fluorescence resonance energy transfer (FRET), such as the cyanine dyes noted above.

A "mismatched nucleotide" or a "mismatch" refers to a nucleotide that is not complementary to the target sequence at that position or positions. An oligonucleotide probe may have at least one mismatch, but can also have 2, 3, 4, 5, 6 or 7 or more mismatched nucleotides.

The term "polymorphism" as used herein refers to an allelic variant. Polymorphisms can include single nucleotide polymorphisms (SNPs) as well as simple sequence length polymorphisms. A polymorphism can be due to one or more nucleotide substitutions at one allele in comparison to another allele or can be due to an insertion or deletion, duplication, inversion and other alterations known to the art.

The term "modification" as used herein refers to alterations of the oligonucleotide probe at the molecular level (e.g., base moiety, sugar moiety or phosphate backbone). Nucleoside modifications include, but are not limited to, the introduction of cleavage blockers or cleavage inducers, the introduction of minor groove binders, isotopic enrichment, isotopic depletion, the introduction of deuterium, and halogen modifications. Nucleoside modifications may also include moieties that increase the stringency of hybridization or increase the melting temperature of the oligonucleotide probe. For example, a nucleotide molecule may be modified with an extra bridge connecting the 2' and 4' carbons resulting in locked nucleic acid (LNA) nucleotide that is resistant to cleavage by a nuclease (as described in Imanishi et at, U.S. Pat. No. 6,268,490 and in Wengel et al., U.S. Pat. No. 6,794,499). The compositions of the tag portion of the oligonucleotide probe and of the quenching oligonucleotide molecule are only restricted by their ability to form stable duplexes. These oligonucleotides can therefore comprise of DNA, L-DNA, RNA, L-RNA, LNA, L-LNA, PNA (peptide nucleic acid, as described in Nielsen et al., U.S. Pat. No. 5,539,082), BNA (bridged nucleic acid, for example, 2',4'-BNA(NC) [2'-O,4'-C-aminomethylene bridged nucleic acid] as described in Rahman et al., J. Am. Chem. Soc. 2008;130(14):4886-96), L-BNA etc. (where the "L-XXX" refers to the L-enantiomer of the sugar unit of the nucleic acids) or any other known variations and modifications on the nucleotide bases, sugars, or phosphodiester backbones.

Other examples of nucleoside modifications include various 2' substitutions such as halo, alkoxy and allyloxy groups that are introduced in the sugar moiety of oligonucleotides. Evidence has been presented that 2'-substituted-2'-deoxyadenosine polynucleotides resemble double-stranded RNA rather than DNA. Ikehara et al. (Nucleic Acids Res., 1978, 5, 3315) have shown that a 2'-fluro substituent in poly A, poly I, or poly C duplexed to its complement is significantly more stable than the ribonucleotide or deoxyribonucleotide poly duplex as determined by standard melting assays. Inoue et al. (Nucleic Acids Res., 1987, 15, 6131) have described the synthesis of mixed oligonucleotide sequences containing 2'-OMe (O-methyl) substituents on every nucleic nucleotide. The mixed 2'-OMe-substituted oligonucleotide hybridized to its RNA complement as strongly as the RNA-RNA duplex which is significantly stronger than the same sequence RNA-DNA heteroduplex. Examples of substitutions at the 2' position of the sugar include F, CN, $CF_3$, $OCF_3$, OMe, OCN, O-alkyl, S-alkyl, SMe, $SO_2Me$, $ONO_2$, $NO_2$, $NH_3$, $NH_2$, NH-alkyl, $OCH_3=CH_2$ and OCCH.

The term "specific" or "specificity" in reference to the binding of one molecule to another molecule, such as a probe for a target polynucleotide, refers to the recognition, contact, and formation of a stable complex between the two molecules, together with substantially less recognition, contact, or complex formation of that molecule with other molecules. As used herein, the term "anneal" refers to the formation of a stable complex between two molecules. In particular, "anneal" can refer to formation of a stable double-stranded complex between complementary oligonucleotides.

A probe is "capable of annealing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, 95% or 99%, and most preferably 100%. For the purpose of determining sequence identity of a DNA sequence and a RNA sequence, U and T often are considered the same nucleotide. For example, a probe comprising the sequence ATCAGC is capable of hybridizing to a target RNA sequence comprising the sequence GCUGAU.

The term "cleavage agent" as used herein refers to any means that is capable of cleaving an oligonucleotide probe to yield fragments, including but not limited to enzymes. For methods wherein amplification does not occur, the cleavage agent may serve solely to cleave, degrade or otherwise separate the second portion of the oligonucleotide probe or fragments thereof. The cleavage agent may be an enzyme. The cleavage agent may be natural, synthetic, unmodified or modified.

For methods wherein amplification occurs, the cleavage agent is preferably an enzyme that possesses synthetic (or polymerization) activity and nuclease activity. Such an enzyme is often a nucleic acid amplification enzyme. An example of a nucleic acid amplification enzyme is a nucleic acid polymerase enzyme such as *Thermus aquaticus* (Taq) DNA polymerase or *E. coli* DNA polymerase I. The enzyme may be naturally occurring, unmodified or modified.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable DNA polymerase" refers to a DNA polymerase that is stable (i.e., resists breakdown or denaturation) and retains sufficient catalytic activity when subjected to elevated temperatures for selected periods of time. For example, a thermostable DNA polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). Examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, *Thermos thermophilus* DNA polymerase, and the like.

A "modified" polymerase refers to a polymerase in which at least one monomer differs from the reference sequence, such as a native or wild-type form of the polymerase or another modified form of the polymerase. Such modified polymerases are described in, for example, U.S. Patent Publication Nos. 20110294168A1 and 20140178911A1. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified polymerases include G46E E678G CS5 DNA polymerase, G46E L329A E678G CS5 DNA polymerase, G46E L329A D640G 567W CS5 DNA polymerase, G46E L329A D640G 567W E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not. Some enzymes that have 5' to 3' nuclease activity are 5' to 3' exonucleases. Examples of such 5' to 3' exonucleases include: exonuclease from *B. subtilis*, phosphodiesterase from spleen, Lambda exonuclease, exonuclease TT from yeast, exonuclease V from yeast, and exonuclease from *Neurospora crassa*.

The term "propanediol" or "propanediol spacer" refers to 1,3-propanediol and is synonymous with propane-1,3-diol, 1,3-dihydroxypropane, and trimethylene glycol. The term "HEG" or "HEG spacer" refers to hexaethylene glycol, which is synonymous with 3,6,9,12,15-pentaoxaheptadecane-1,17-diol.

Various aspects of the present invention are based on a special property of nucleic acid polymerases. Nucleic acid polymerases can possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur efficiently, an upstream oligonucleotide must also be annealed to the same larger polynucleotide.

The detection of a target nucleic acid utilizing the 5' to 3' nuclease activity can be performed by a "TaqMan® assay" or "5'-nuclease assay", as described in U.S. Pat. Nos. 5,210,015; 5,487,972; and 5,804,375; and Holland et al., 1988, Proc. Natl. Acad. Sci. USA 88:7276-7280. In the TaqMan® assay, labeled detection probes that hybridize within the amplified region are present during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in a 5' nuclease assay. Often, the detection probe is labeled with two fluorescent dyes, one of which (a "quencher" or "quenching moiety") is capable of quenching the fluorescence of the other dye (a "reporter" or "reporter moiety"). The dyes are attached to the probe, typically with the reporter or detector dye attached to the 5' terminus and the quenching dye attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673 describe alternative methods for detecting the degradation of probe which occurs concomitant with amplification.

A 5' nuclease assay for the detection of a target nucleic acid can employ any polymerase that has a 5' to 3' exonuclease activity. In some embodiments, the polymerases with 5'-nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*, as well as chimeric forms thereof. For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, and *Thermus* species sps17 (sps17) DNA polymerase (e.g., described in U.S. Pat. Nos. 5,405,774; 5,352,600; 5,079,352; 4,889,818;.5,466,591; 5,618,711; 5,674,738, and 5,795,762). *Thermatoga* polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/U.S. 91/07035 with Publication No. WO 92/06200. The sequence of *Thermatoga neapolitana* may be found in International Patent Publication No. WO 97/09451.

In the 5' nuclease assay, the amplification detection is typically concurrent with amplification (i.e., "real-time"). In some embodiments the amplification detection is quantitative, and the amplification detection is real-time. In some embodiments, the amplification detection is qualitative (e.g., end-point detection of the presence or absence of a target nucleic acid). In some embodiments, the amplification detection is subsequent to amplification. In some embodiments, the amplification detection is qualitative, and the amplification detection is subsequent to amplification.

Tags Probes

The novel probes used in the present invention have two distinguishing features. The first feature of the TAGS probe is that it comprises two distinct portions. The first portion is referred as an annealing portion and comprises a sequence that is at least partially complementary to a target nucleic acid sequence, such that it is capable of hybridizing to the target sequence. The annealing portion also contains a quencher moiety. In one embodiment, the annealing portion further contains a reporter moiety, such as a fluorescent dye, that is capable of being quenched by the quencher moiety and is separated from the quencher moiety by a nuclease susceptible cleavage site. The second portion of the oligonucleotide probe is referred as a tag portion. The tag portion is attached to the strand of the annealing portion that bears the reporter moiety and the quencher moiety. In one embodiment, the tag portion is attached to the 5' terminus of the annealing portion. In another embodiment, the tag portion is attached to the 3' terminus of the annealing portion. In another embodiment, the tag portion is attached anywhere between the 5' terminus and the 3' terminus of the annealing portion via a linker. The tag portion may comprise a nucleotide sequence that is not complementary to the target nucleic acid sequence and forms a "flap" region that is not capable of binding to the target nucleic acid (see FIG. 1 for a graphical representation of a 5' flap probe). The tag portion may also be comprised of non-nucleotides such as any organic moieties, or repeat units (e.g. $(CH_2—CH_2—O)n$, etc.) as long as it can be attached to the annealing portion and can interact with a quenching molecule (as described in the following section). In one embodiment, the tag portion contains a reporter moiety such as a fluorescent dye that is capable of being quenched by the quencher moiety on the annealing portion. The annealing and tag portions of the oligonucleotide probe may optionally be separated by a non-nucleotide "linker". This linker can be comprised of carbon, carbon and oxygen, carbon and nitrogen, or any combination of these and can be of any length. Furthermore, the linker can be comprised of a linear moiety or a cyclic moiety. The linker may be derived from a single unit or from multiple identical or different units separated by phosphate linkages. The purpose of the linker is to create a region at the junction of the annealing and tag portions of the oligonucleotide probe. When the tag portion is separated from the annealing portion, the linker may also prevent the tag portion from being extended by a nucleic acid polymerase. Alternatively, another modification on the separated tag portion renders it non-extendible by the nucleic acid polymerase.

The second feature of the novel probe is that the tag portion binds to a quenching molecule, such as an oligonucleotide. If the tag portion is a nucleotide sequence, the quenching molecule may be an oligonucleotide that is fully or partially complementary to the nucleotide sequence of the tag portion and hybridizes to the tag portion. The quenching molecule also contains or is associated with a quencher moiety, i.e. a second quencher moiety, which is also capable of quenching the signal from the reporter moiety (e.g. fluorescent dye) on the tag portion. The quencher moiety on or associated with the quenching molecule (the second quencher moiety) can be the same as or different from the quencher moiety on the annealing portion (the first quencher moiety). Therefore, prior to performing PCR amplification, the reporter moiety on the tag portion is quenched by both the quencher moiety on the annealing portion of the probe and by the quencher moiety on or associated with the quenching molecule (e.g. by a quenching oligonucleotide as shown in FIG. 1).

Use of TAGS Probes in Conventional PCR Thermocycling Instruments

The general principle of using the novel probe to perform real-time PCR amplification and detection of target nucleic acid in a conventional PCR thermocycler is described below. First, a sample suspected of containing the target nucleic acid is provided. The sample is then contacted inside a single reaction vessel (e.g., a single test tube or a single well in a multi-well microplate) with PCR reagents that contain both the oligonucleotide primers capable of generating amplicons of the target nucleic acid and the novel oligonucleotide probe. PCR amplification begins by using a nucleic acid polymerase having 5' to 3' nuclease activity such that during the extension step of each PCR cycle, the nuclease activity of the polymerase allows cleavage and separation of the tag portion from the quenching moiety on the annealing portion of the probe. The separated tag portion may optionally contain a modification (such as the non-nucleotide linker) such that it is not capable of being extended by a nucleic acid polymerase.

Next, the signal from the reporter moiety on the separated tag portion is measured at a first temperature, usually, the annealing and/or extension temperature, at which the quenching molecule is still bound to the tag portion. Due to the presence of the quencher moiety on or associated with the quenching molecule, the signal from the reporter moiety (e.g. a fluorescent dye) on the tag portion is still quenched.

Figure 2:
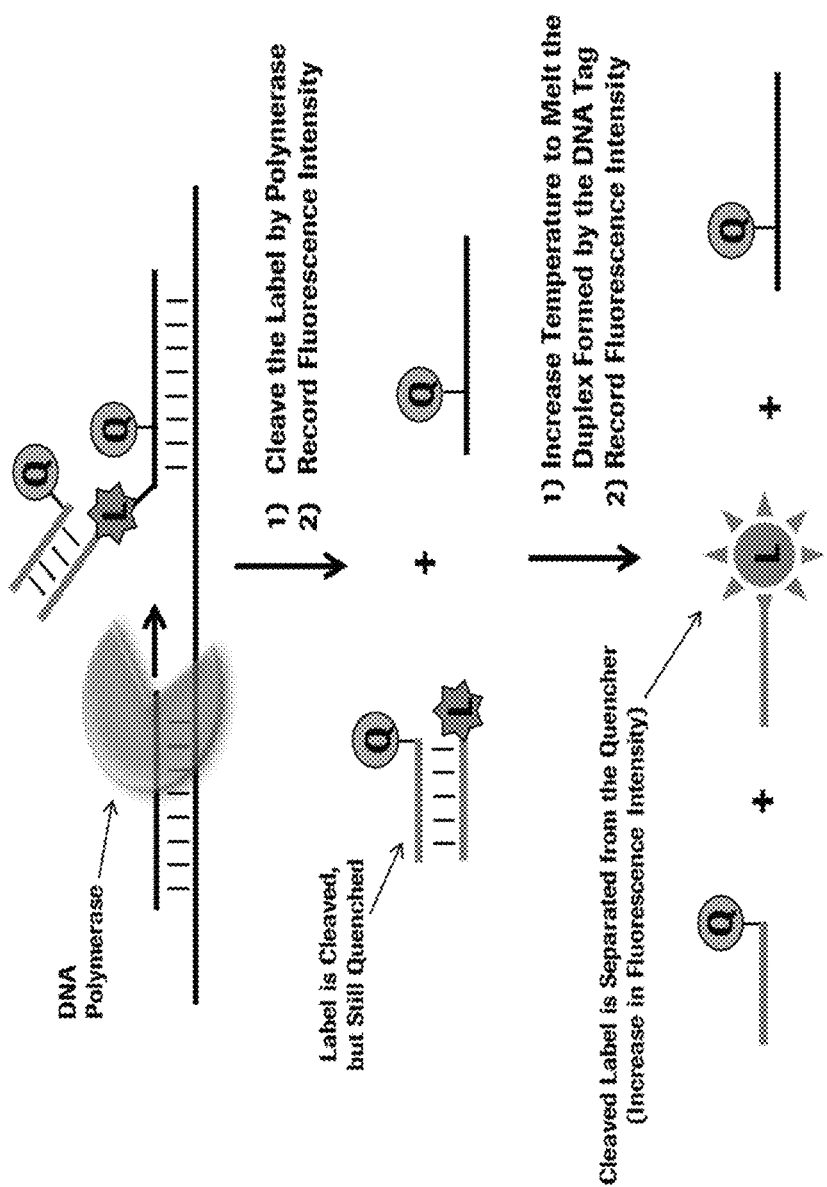
FIG. 2 is a graphical representation of a real-time PCR method using a TAGS probe, that shows the separation of the tag portion and subsequent dissociation of the quenching oligonucleotide during the PCR.
Figure 3:
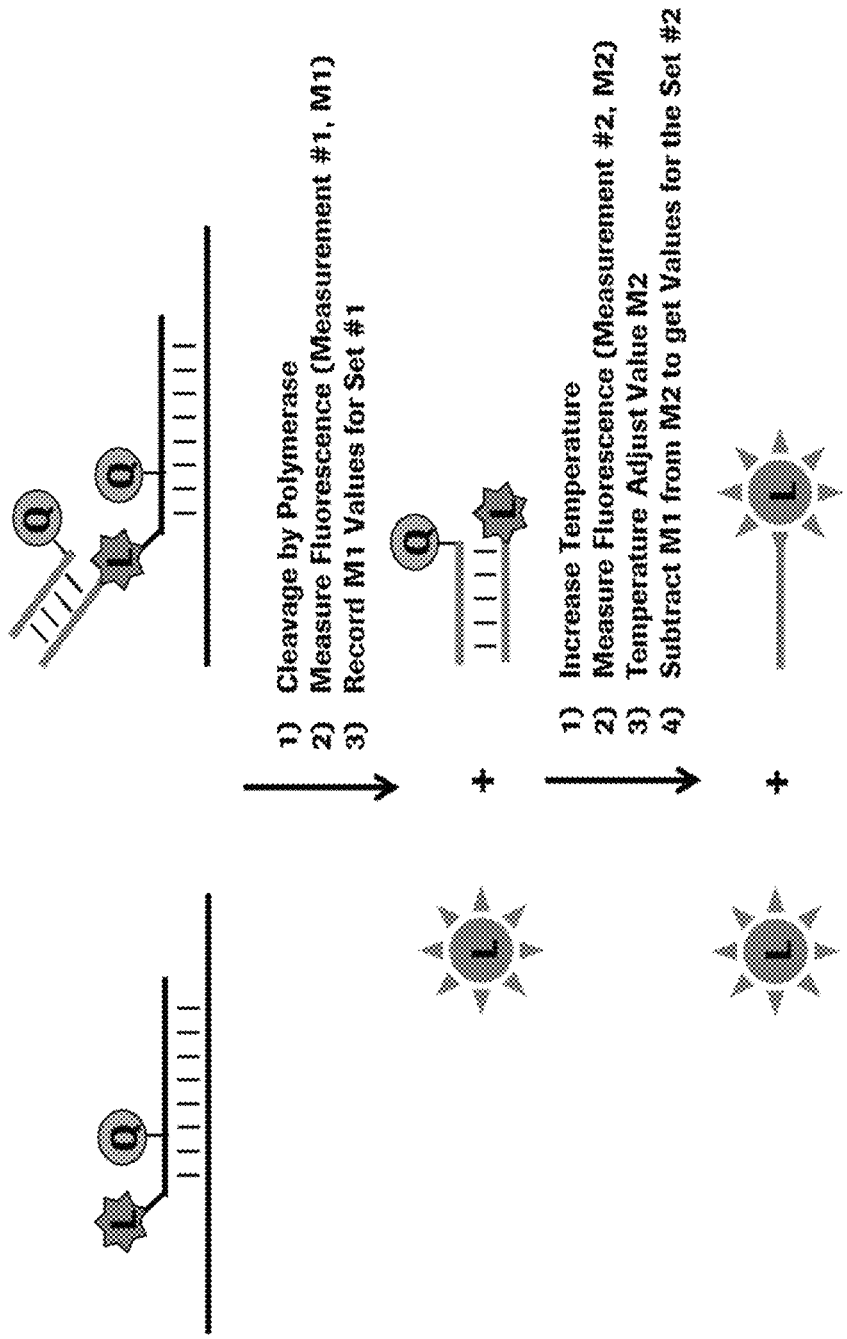
FIG. 3 is a graphical representation of a real-time PCR method using a TAGS probe, that shows the fluorescence detection step and subsequent calculation steps.

Then, as a normal step in a PCR cycle, the temperature is gradually raised to the denaturation temperature. As the temperature increases from the extension temperature to the denaturation temperature, a temperature point is reached at which the quenching molecule is no longer bound to the tag portion. If the quenching molecule is an oligonucleotide that has sequences complementary to the nucleotide sequence of the tag portion, this dissociation occurs at the melting temperature (Tm) of the duplex formation between the quenching oligonucleotide molecule and the tag. portion. Signal from the reporter moiety which is no longer quenched by the quencher moiety on or associated with the quenching oligonucleotide is then measured at a second temperature that is at or above the Tm temperature of the duplex. In fact, it may be better that the second temperature is above the Tm temperature to ensure that close to 100% of the tag portion ate in single-stranded form. However, it is also possible to measure the signal at a temperature below the Tm temperature. Then, a calculated signal value is determined by subtracting the signal detected at the first temperature when the quenching molecule is still bound to the tag, portion from the signal detected at the second temperature when the quenching molecule is not bound to the tag portion (see FIG. 2 and FIG. 3). The calculated signal value may optionally be normalized for correction of signals that may be affected by temperature. For example, fluorescent signals are known to decrease at higher temperatures, and therefore, standards can be used to normalize the signal values obtained at different temperatures.

These signal measurements and calculations are performed at multiple PCR cycles and the determined cumulative signal values can be used to determine not only the presence or absence but also the quantity of the target nucleic acid by determining the threshold value (Ct value) from a PCR growth curve generated from the signal values calculated plotted against PCR cycle number. In one embodiment, the signal measurements and calculations are performed at each PCR cycle.

Figure 4:
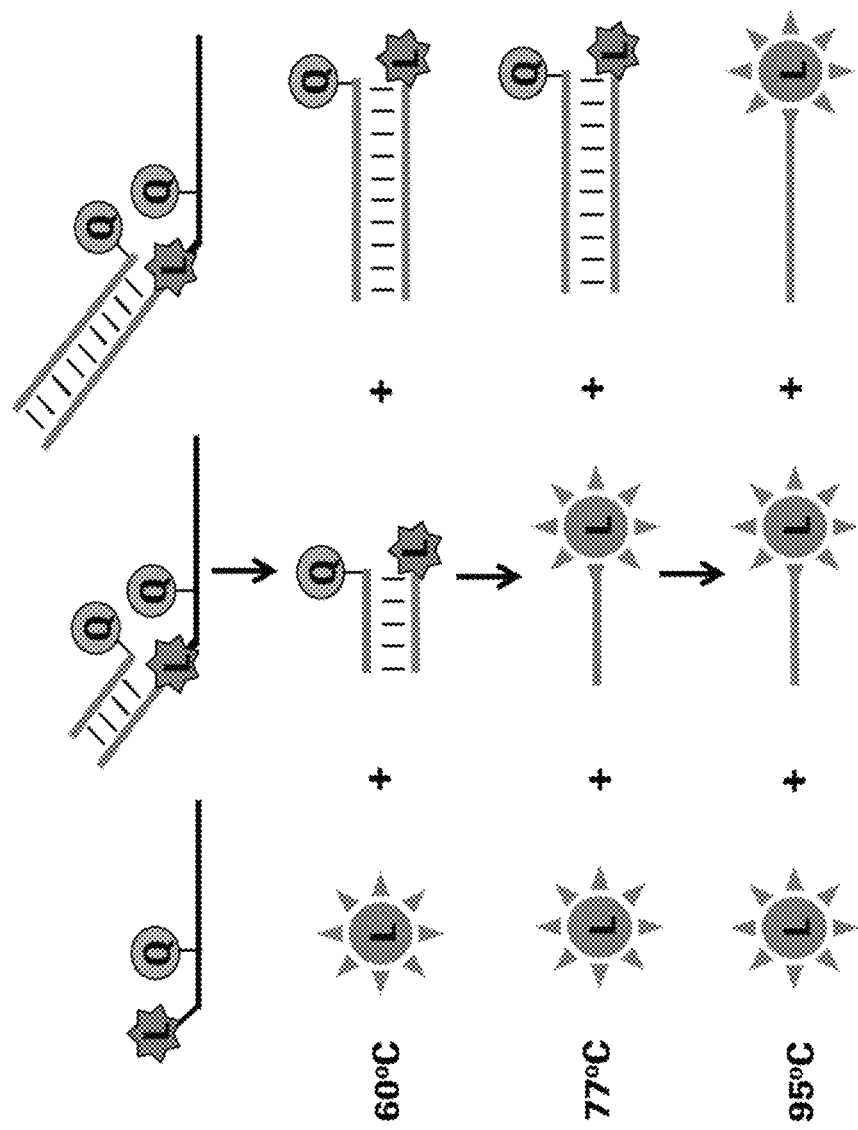
FIG. 4 is a graphical representation of a real-time PCR method using a TAGS probe, that shows the effects of temperature on the cleaved tag portions of the probe when hybridized to a quenching oligonucleotide.

Multiplex PCR assays using only one reporter moiety (e.g. one fluorescent dye) is possible by designing oligonucleotide probes that have tag portions hybridized to their respective quenching oligonucleotide molecules at various melting temperatures. For example, amplification and detection of three target nucleic acid in one reaction can be achieved by using three oligonucleotide probes all labeled with the same fluorophore. A standard TaqMan® oligonucleotide probe may be used to detect the first target by measuring the fluorescent signal at a first temperature (usually the annealing temperature of a PCR cycle). A first TAGS probe with a low Tm tag-quenching oligonucleotide duplex may be used to detect the second target by measuring the calculated fluorescent value at a second temperature at or above its Tm temperature and that is higher than the first temperature. A second TAGS probe with a high Tm tag-quenching oligonucleotide duplex may be used to detect the third target by measuring the calculated fluorescent value at a third temperature at or above its Tm temperature and that is higher than the second temperature. (see FIG. 4) Theoretically, it would be possible to use one TaqMan® probe and two different TAGS probes with four to seven different reporter moieties (e.g. fluorescent dyes) to detect between 12 and 21 different target nucleic acids in one reaction or one TagMan® probe and 3 different TAGS probes to detect between 16 and 28 different target nucleic acids in one reaction.

Additionally, the novel probes of the present invention can be designed such that the tag portion is a nucleotide sequence and is connected to a quenching oligonucleotide to form a hairpin (i.e. a stem-loop structure). In this structure, the "stem" portion will consist of the complementary regions between the tag portion and the quenching oligonucleotide while the "loop" portion may be comprised of non-complementary nucleotides or non-nucleotides such as linkers as previously described.

Figure 5:
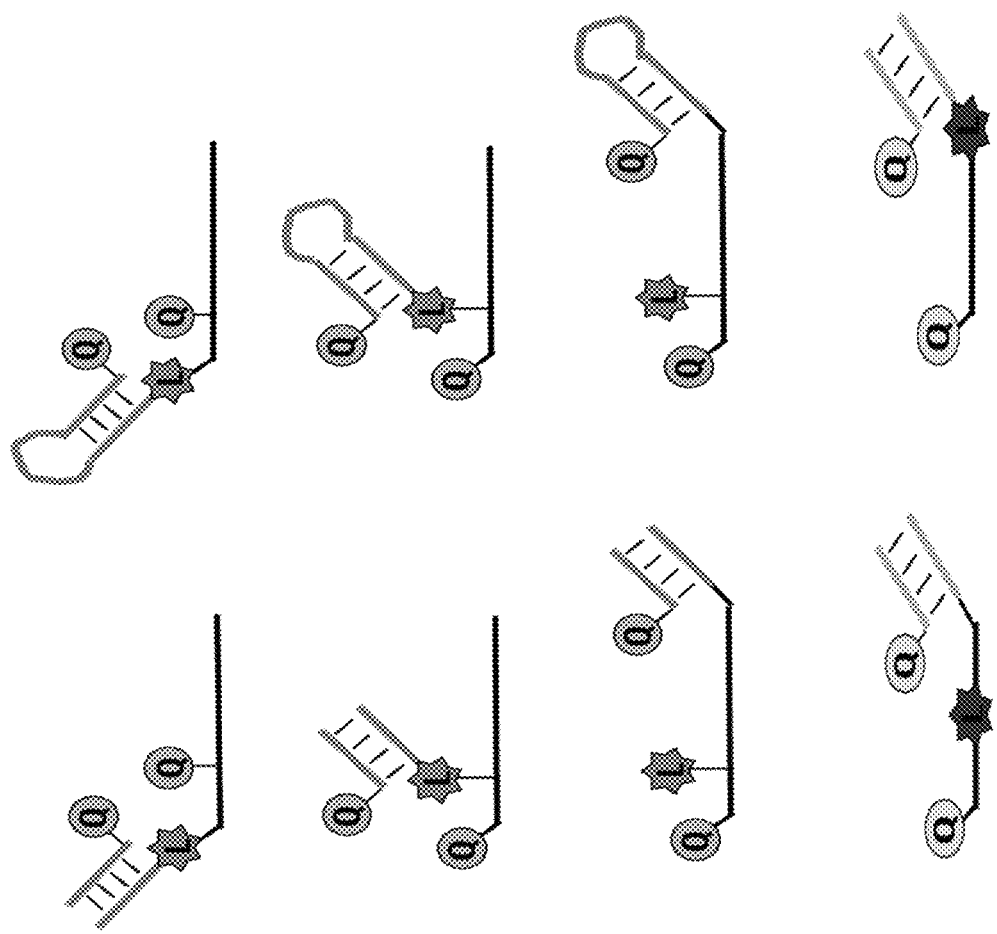
FIG. 5 shows different embodiments of the oligonucleotide probes used to practice the methods of the present invention.

Although the novel probes of the present invention have been described as having the reporter moiety located on the tag portion of the probes, it is also possible to position the reporter moiety on the annealing portion and place the first quencher moiety on the tag portion, as long as the reporter moiety can reversibly interact with the second quencher moiety on the quenching molecule. In a general sense, the reporter moiety is designed and positioned in the probe oligonucleotide in such a way that it is separated from the first quenching moiety on the annealing portion during the 5' nuclease (TaqMan®) assay and further designed to reversibly interact with the second quenching moiety on the quenching molecule. Some of these various alternate embodiments of the novel probes can be seen in FIG. 5.

In order to practice the methods of the present invention, certain features are necessary in the design of the tag portion of the probe oligonucleotide and of the quenching molecule. In one embodiment, both the tag portion and the quenching molecule are comprised of nucleotide sequences. In this situation, both the tag portion and the quenching oligonucleotide should not hybridize specifically to the target nucleic acid sequence but they should be fully or partially complementary to each other to allow hybridization at the desired temperatures. Both may include a modification at their 3' termini in order to not be extended by the nucleic acid polymerase during PCR amplification. Both the reporter moiety (e.g. fluorescent dye) on the tag portion and the quencher moiety on the quenching oligonucleotide can be located at the 5' terminus, the 3' terminus or at any position between the 5' and 3' termini but they must be located in proximity to each other when the tag portion is hybridized to the quenching oligonucleotide to allow the quenching moiety to quench the detectable signal from the reporter moiety.

With respect to different tag portions being hybridized to their respective quenching oligonucleotide molecules at various Tm temperatures, modified nucleotides can be introduced at all or some positions on either the tag portions, on the quenching oligonucleotides or on both the tag portions and the quenching oligonucleotides such that oligonucleotide length can be shortened. Examples of nucleotide modifications that serve to alter the oligonucleotide melting temperature include LNA, PNA, G-clamp (9-(aminoethoxy)-phenoxazine-2'-deoxycytidine), propynyl deoxyuridine (pdU), propynyl deoxycytidine (pdC), and various 2' modifications at the sugar group, such as 2'-O-methyl modifications. Another type of modification that may serve to prevent the unwanted binding of nucleic acid polymerase to the tag portion or to the quenching oligonucleotide would include the use of enantiomeric L-form of a nucleotide, such as L-DNA, L-RNA or L-LNA.

In another embodiment, the tag portion of the oligonucleotide probe and the quenching molecule are comprised of non-nucleotide molecules that reversibly interact with each other in a temperature-dependent manner. Examples of such non-nucleotide interactions include but are not limited to protein-protein interactions, protein-peptide interactions (e.g. peptide aptamers), protein-small molecule interactions, peptide-small molecule interactions, small molecule-small molecule interactions. In one example, the well-known interaction between biotin and avidin (or streptavidin) can be exploited by modifying either the biotin moiety (e.g. desthiobiotin) or the avidin moiety (see, Nordlund et at, J. Biol. Chem., 2003, 278 (4) 2479-2483) or both in order to make the interaction reversible and temperature dependent.

In yet another embodiment, the interaction between the tag portion and the quenching molecule may involve interaction between a nucleotide sequence (or nucleotide sequences) and a non-nucleotide molecule in a sequence-specific manner. Examples of these types of interactions include but are not limited to nucleic acid aptamers, DNA binding proteins or peptides and DNA minor groove binders. The design and synthesis of sequence-specific DNA-binding molecules have been described in several papers (see e.g. Dervan, Science, 1986, 232, 464-471; White et al., Nature, 1998, 391, 468-471) and these methods may be used to generate interactions between the tag portion and the quenching molecule that are temperature-dependent. Similarly, interactions between double stranded nucleotides and soluble quenchers can also be explored such that the quenching moiety does not need to be contained within the quenching molecule itself but may be in a soluble foim that will interact with and quench the reporter moiety only when the tag portion is bound to the quenching molecule.

The Use of TAGS Probes in a Multi-Segment Tubule PCR System

The present disclosure also describes multi-segment tubule PCR devices, consumables, and methods for processing samples using such devices and consumables. An example of such a system is the cobas® LIAT® PCR System (Roche Molecular Systems, Pleasanton, Calif.).

The cobas® Liat® System is comprised of the Liat® tube and Liat® analyzer (instrument). The assay utilizes a single-use disposable Liat® tube that holds the sample preparation and RT-PCR reagents, and facilitates the sample preparation and RT-PCR processes. The Liat® tube contains all required unit dose reagents pre-packed in tube segments, separated by frangible seals, in the order of reagent use.

The Liat® analyzer automates and integrates sample preparation, nucleic acid amplification, detection and quantitation of the target sequence in biological samples. The Liat® analyzer performs all assay steps from clinical sample and reports assay result automatically. During the testing process, multiple sample processing actuators of the analyzer compress the Liat® tube to selectively release reagents from tube segments, move the sample from one segment to another, and control reaction volume, temperature, and time to conduct sample preparation, nucleic acid extraction, target enrichment, inhibitor removal, nucleic acid elution and real-time PCR. An embedded microprocessor controls and coordinates the actions of these actuators to perform all required assay processes within the closed Liat® tube. To run the assay, a user loads sample into a Liat® tube and places the loaded Liat® tube into a Liat® analyzer. The analyzer will perform sample preparation, RT-PCR, result calculation and report. All the processes are controlled by the assay script.

The part of the assay script that controls the thermocycling profile is shown in Table 1 below. In this embodiment, fluorescence readings from the PAM label were taken at 58° C. and at a high temperature for each cycle beginning from cycle #6. One of skill in the art would recognize that the parameters described in Table 1 may be changed as necessary, e.g., temperatures, durations, and number of cycles all may be altered as needed.

TABLE 1

| Steps | Temperature (° C.) | Time (seconds) | Cycle (number) |
|---|---|---|---|
| RT | 55 | 30 | 1 |
|  | 60 | 60 |  |
|  | 65 | 115 |  |
| PCR-1 | 95 | 5 | 5 |
|  | 55 | 5 |  |
|  | 58 | 5 |  |
|  | 60 | 5 |  |
| PCR-2 | 94 | 4 | 40 |
|  | 58 | 4 |  |
|  | 58 | 12 + 0.086/cycle |  |

In several embodiments, segmented tubules provide a convenient vessel for receiving, storing, processing, and/or analyzing a biological sample. In certain embodiments, the is segmented tubule facilitates sample processing protocols involving multiple processing steps. In certain embodiments, a sample may be collected in a sample tubule, and the tubule then positioned in an analyzer; the analyzer may then manipulate the tubule and its contents to process the sample.

In one embodiment, a flexible tubule may be segmented into compartments by breakable seals. The individual segments may contain various reagents and buffers for processing a sample. Clamps and actuators in an analyzer may apply, hold, and/or release force to the tubule in various combinations and with various timings to direct the movement of fluid and to cause the breakable seals to burst. This bursting of the breakable seals may create an inner tubule surface that is substantially free of obstructions to fluid flow. In some embodiments, the flow of the biological sample may be directed toward the distal end of the tubule as the processing progresses, while the flow of waste may be forced to move in the opposite direction, toward the opening of the tubule where the sample was initially input. This sample inlet can be sealed, optionally permanently, by a cap with a locking mechanism, and a waste chamber may be located in the cap to receive the waste for storage. A significant benefit of this approach is that the processed sample does not come into contact with surfaces that have been touched by the unprocessed sample. Consequently, trace amounts of reaction inhibitors present in the unprocessed sample that might coat the walls of the tubule are less likely to contaminate the processed sample.

In some embodiments the tubule may be so expandable as to be capable of receiving a volume of fluid from each of multiple segments in one segment; this can allow sample and reagents to undergo certain processing steps in one segment leading to a simpler mechanical structure for performing assays. Another benefit of an embodiment using a tubule that may be so expandable is that the same tubule structure may be used to package different volumes of reagents within segments, allowing the same tubule to be packaged in differing ways depending upon the assay to be performed.

Referring to FIGS. 13A-B, FIGS. 14A-B, 15A-B, 16A-B, and 17A-B, a transparent flexible tubule 10 is capable of being configured into a plurality of segments, such as 16, 110, 120, 130, 140, 150, 160, 170, 180, and/or 190, and being substantially flattened by compression. In an embodiment, a flexible tubule may have at least two segments. The flexible tubule can provide operational functionality between approximately 2° C. and 105° C., compatibility with samples, targets and reagents, low gas permeability, minimal fluorescence properties, and/or resilience during repeated compression and flexure cycles. The tubule may be made of a variety of materials, examples of which include but are not limited to: polyolefins such as polypropylene or polyethylene, polyurethane, polyolefin co-polymers and/or other materials providing suitable characteristics. The tubule properties, such as transparency, wetting properties, surface smoothness, surface charge and thermal resilience, may affect the performance of the tubule. These properties may be improved through such exemplary processes as: seeding, plasma treating, addition of additives, and irradiation. In some embodiments, an additive material may be added to the plastic to improve selected characteristics. For example, a slip additive may be added, such as erucamide and/or oleamide; in some embodiment, a so-called "anti-block" additive may be added. An additive may have a concentration in the plastic in the range from about 0.01% to about 5.0%.

The tubule may be manufactured by a wide variety of suitable methods such as extrusion, injection-molding and blow-molding. In one embodiment, the tubule is continuously extruded. Alternative techniques for manufacturing the tubule include, e.g., casting, extruding or blowing films that can be fashioned by secondary processing operations into a suitable tubule. The tubule wall material may include multiple layers by co-extrusion, or by film lamination. For example, an inner layer may be chosen for high biocompatibility and an exterior layer may be chosen for low gas permeability. As a further example, the interior layer may be readily formed into a breakable seal 14 (FIG. 14A-B and FIGS. 15A-B), such as a peelable seal, while the exterior layer may be resilient and highly impermeable. For example, the tubule may have a wall thickness of about 0.03 mm to about 0.8 mm, preferably 0.03 mm to about 0.5 mm, with the tubule able to be substantially flattened with an applied exterior pressure on the order of one atmosphere.

Figure 19A:
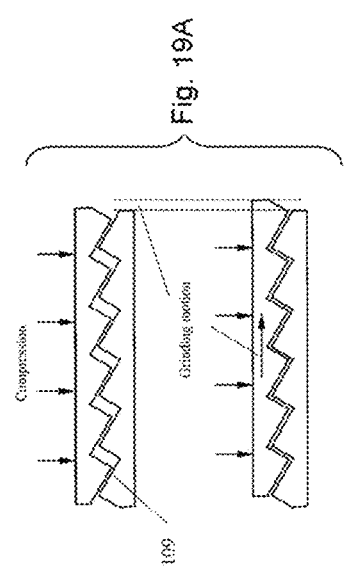
FIGS. 19A-B are, respectively, cross sectional and perspective views of exemplary embodiments of grinding systems.

In some embodiments, the apparatus may have toughened walls in at least one segment to allow for the dislocation of clumps of cells from solid sample such as biopsy samples or solid environmental samples using grinding motions. An example of these toughened wall features, as illustrated in FIG. 19A, can be micro-teeth-like inner surfaces on opposing faces of the tubule wall, which are offset such that compressing the tubule produces a sliding motion along the axis of the tubule. The tubule wall in the vicinity of these grinding surfaces 109 may be fortified using reinforcement patches made of a suitably resilient plastic such as polycarbonate or polyethylene terephthalate. The teeth-like inner surfaces may be made of similarly suitable materials. In another embodiment, a pad, such as 214 illustrated in FIGS. 17A-B, having grinding surface feature can be attached on the inner wall of tubule. The pad can be made by toughened material, and the surface feature can be created by using conventional mechanical, electrochemical or microelectromechanical methods, so that the pad can endure compression.

Referring to FIG. 14A and FIGS. 15A-B, in certain embodiments, the segments of the sample tubule 10 are defined by breakable seals 14 to fluidly isolate adjacent segments. This seal feature can be useful in separating, for example, a dry reagent from a liquid reagent until the two can be reconstituted to perform a specific assay, or for separating chemically reactive species until the reaction is desired. As illustrated in FIGS. 15A-B, a breakable seal 14 may be formed in a region of the tubule 10 where opposing walls have been substantially joined, but not joined so strongly as to prevent the walls from being later peeled apart without significantly marring, the tubule or the previously sealed surfaces. Such a seal may be termed a "peelable" seal. In some embodiments, the peelable seal region may be a band orthogonal to the axis of the tubule. It may span a tubule length in the range of about 0.5 mm to 5 mm, or about 1 mm to about 3 mm, most preferably about 1 mm. The seal preferably spans the entire width of the tubule so as to seal the segment. In some embodiments, the seal band may vary in height or shape and/or be oriented at an angle transverse to the axis of the tubule; such variations can change the peel characteristics.

Breakable seals 14, in the form of peelable seals, can be created between opposing walls of the tubule by applying a controlled amount of energy to the tubule in the location where the peelable seal is desired. For example, a temperature controlled sealing head can press the tubule at a specific pressure against a fixed anvil for a specific time interval. Various combinations of temperature, pressure and time may be selected to form a seal of desired size and peel strength. Energy may be delivered, for example, by a temperature controlled sealing head maintained at a constant temperature between 105° C. and 140° C. to heat a polypropylene tubing material; an actuator capable of delivering a precise pressure between 3 and 100 atmospheres over the desired seal region; and a control system to drive the sequencing of the actuator to a specific cycle time between 1 and 30 seconds. Using this method, satisfactory seals have been created in polypropylene tubules to peel open when subjected to an internal pressure on the order of 1 atmosphere. Alternate techniques to deliver the sealing energy to the tubule include RP and ultrasonic welding.

In other embodiments, alternate tubule materials and blends of materials can be used to optimize peelable seal performance. For example, two polypropylene polymers of differing melting temperature can be blended in a ratio such that the composition and melt characteristics are optimized for peelable seal formation. Referring to FIG. 13B, in addition to or in lieu of breakable seals 14, the flexible tubule can further have one or more pressure gates 194, which are capable of reversibly opening and closing during the operation of a test by applying a controlled force to a segment of the flexible tubule.

A filter can be embedded in a tubule segment. Examples of filters 206 and 216 are shown in FIG. 16A and FIGS. 17A-B, respectively. In a preferred embodiment, a filter can be formed by stacking multiple layers of flexible filter material. The uppermost layer of the filter that directly contacts a sample may have a pore size selected for filtration; the bottom layer of the filter may include a material with much larger pore size to provide a support structure for the uppermost layer when a pressure is applied during filtration. In this preferred embodiment, the filter may be folded to form a bag, with the edges of its open end firmly attached to the tubule wall. The segment with the filter bag may be capable of being substantially flattened by compressing the exterior of the tubule.

In exemplary embodiments, one or more reagents can be stored either as dry substance and/or as liquid solutions in tubule segments. In embodiments where reagents may be stored in dry format, liquid solutions can be stored in adjoining segments to facilitate the reconstitution of the reagent solution. Examples of typical reagents include: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. in embodiments where one of the reagents is a chaotropic salt solution, a preferred component is guanidinium isocyanate or guanidinium hydrochloride or a combination thereof. In some embodiments, the order in which reagents may be stored in the tubule relative to the opening through which a sample is input, reflects the order in which the reagents can be used in methods utilizing the tube. In some embodiments, a reagent includes a substance capable of specific binding to a preselected component of a sample. For example; a substance may specifically bind to nucleic acid, or a nucleic acid probe may specifically bind to nucleic acids having particular base sequences.

In other embodiments, a solid phase substrate can be contained within a tubule segment and used to capture one or more selected components of a sample (if such component is present in a sample), such as a target microorganism or nucleic acids. Capturing can help to enrich the target component and to remove reaction inhibitors from a sample. Substrates may be solid phase materials which can capture target cells, virions, nucleic acids, or other selected components under defined chemical and temperature conditions, and may release the components under different chemical and temperature conditions.

In some embodiments, a reagent can be coated on the substrate. Examples of coatable reagents are: receptors, ligands, antibodies, antigens, nucleic acid probes, peptide nucleic acid probes, phosphothioate nucleic acid probes, bacteriophages, silica, chaotropic salts, proteinases, DNases, RNases, DNase inhibitors, RNase inhibitors, and germinant solutions. in some embodiments, the substrate can be stored in a dry segment of the tubule while in other embodiments it can be stored immersed in a liquid. In some embodiments, the order in which reagents may be stored in the tubule relative to the substrate and the opening through which a sample is input, reflects the order in which the reagents and the substrate can be used in methods utilizing the apparatus.

The substrate can be: beads, pads, filters, sheets, and/or a portion of tubule wall surface or a collection tool. In embodiments where the substrate is a plurality of beads, the beads can be: silica beads, magnetic beads, silica magnetic beads, glass beads, nitrocellulose colloid beads, and magnetized nitrocellulose colloid beads. In some embodiments where the beads can be paramagnetic, the beads can be captured by a magnetic field. Examples of reagents that may permit the selective adsorption of nucleic acid molecules to a functional group-coated surface are described, for example, in U.S. Pat. Nos. 5,705,628; 5,898,071; and 6,534,262. Separation can be accomplished by manipulating the ionic strength and polyalkylene glycol concentration of the solution to selectively precipitate, and reversibly adsorb, the nucleic acids to a solid phase surface.

When these solid phase surfaces are paramagnetic microparticles, the magnetic beads, to which the target nucleic acid molecules have been adsorbed, can be washed under conditions that retain the nucleic acids but not other molecules. The nucleic acid molecules Isolated through this process are suitable for: capillary electrophoresis, nucleotide sequencing, reverse transcription, cloning, transfection, transduction, microinjection of mammalian cells, gene therapy protocols, the in vitro synthesis of RNA probes, cDNA library construction, and the polymerase chain reaction (PCR) amplification. Several companies offer magnetic-based purification systems, such as QIAGEN's MagAttract™, Cortex Biochem's MagaZorb™, Roche Applied Science's MagNA Pure LC™, and MagPrep® Silica from Merck & Co. All of these products use negatively charged particles and manipulate buffer conditions to selectively bind a variety of nucleic acids to the beads, wash the beads and elute the beads in aqueous buffers. Many of the products used by these companies use chaotropic salts to aid in the precipitation of nucleic acids onto the magnetic beads. Examples are described in U.S. Pat. Nos. 4,427,580; 4,483, 920; and 5,234,809.

In some embodiments the substrate may be a pad 214 or 30 (FIGS. 17A-B, FIGS. 18A-C). In further embodiments, the substrate pad can include paper 35, alternating layers of papers 34 with different hydrophobic properties, glass fiber filters, or polycarbonate filters with defined pore sizes. In some embodiments, the pad may be a filter or impermeable sheet 38 for covering selected portion of the surfaces of the pad, the filter having a predetermined pore size. Such a filtration device can be used for separations of white blood cells 32 and red blood cells 33 (or other particles, such as virus or microorganisms) from whole blood 31 and/or other samples. The pad 214 can be mounted on the tubule wall (FIGS. 17A-B) and/or on a sample collection tool 26 (FIGS. 14A-B). in some embodiments the pad can be soaked with a reagent solution while in other embodiments it may be coated with dry reagents.

Preferred exemplary embodiments may include a linear arrangement of 2 or more tubule segments 110, 120, 130, 140, 150, 160, 170, 180, and/or 190 (FIG. 13B). A linear arrangement facilitates moving the sample and resultant waste and target through the tube in a controlled manner. A raw biological sample can be input through a first opening 12 (FIG. 14B) in a first segment 110 (FIG. 13B) of the tubule. Thereafter, waste from a processed sample can be moved back toward the first opening while the target is pushed towards the opposite end, thereby minimizing contamination of the target by reaction inhibitors that may have become attached to the tubule wall, and confining the target to a clean segment of the tubule which can contain suitable reagents for further operations of the target. Some embodiments may use a plurality of at least three segments, each containing at least one reagent. In some embodiments, these segments may contain reagents in the following order: the reagent in the second segment may be either a lysis reagent, a dilution or wash buffer, or a substrate; the reagent in the third segment may be either a substrate, a lysis reagent, a washing buffer or a neutralization reagent; the reagent in the fourth segment may be a wash buffer, a suspension buffer, an elution reagent, or nucleic acid amplification and detection reagents. In some embodiments, the three segments may be arranged continuously, while in other embodiments, these three segments may be separated by another segment or segments in between via breakable seals.

In some embodiments, a pressure gate 194 (FIG. 13B) can be incorporated to selectively close and open a second opening, located at the distal end of the tubule, to collect the products generated during a test from the tubule for further processing, outside of the tubule. In some embodiments, this second opening may located in a segment 198 defined by two pressure gates 194 and 196 to store a product from the sample processing segments. In some embodiments, a combination of a breakable seal and a pressure gate may be provided for transferring the contents of the tubule to a second opening.

In some embodiments a tube closing device for closing the tube after sample input may include a cap 20 (FIG. 13B) and/or clamp 310. An interface or adaptor 52 between the cap and the first opening of the flexible tubule may be used to ensure a secure, hermetic seal. In an exemplary embodiment, this interface may be threaded and may include tapered features 62 on the cap and/or a suitably rigid tube frame 50 such that, when fastened together, the threads 64 can engage to mate the tapered features 62 between the tube frame and cap to provide a suitable lock. In this exemplary embodiment the cap may require ½ to 1 full rotation to fully remove or attach from the tube holder. The combination of thread pitch and taper angle in the joint can be selected to be both easily manufactured and to provide feedback resistance to inform the user that an effective seal has been created. In other embodiments the cap locking, device may include snap fits, press fits, and/or other types of "twist and lock" mechanism between the cap and tube holder, and similar arrangements in which the cap is permanently attached to the tubule, such as by hinging or tethering the cap.

Both the cap 20 and tube frame 50 can be made of a suitable injection molded plastic such as polypropylene. The tube frame 50 can, in turn, be fastened to the flexible tube by a permanent, hermetic seal. The exterior portion of the cap may be covered with ridges or finger grips to facilitate its handling. Furthermore, the cap 20 may include an area for attaching a sample identification mark or label. As a further alternative, the cap may be directly attached to the first opening flexible tube through a press fit or a collar that compresses the flexible tube opening against a protrusion in the cap to create a hermetic seal. The lock between the tube cap and tube holder may be keyed or guided such that a collection tool 36 or features integrated into the cap can be definitively oriented with respect to the tube to facilitate sample processing and the flattening of the flexible tubule. Furthermore, the cap may incorporate features such as a ratchet or similar safety mechanism to prevent the cap from being removed after it has been installed onto the opening of the flexible tube.

The cap 20 used to close the tubule in some embodiments may contain a cavity 22 within it by making the cap body substantially hollow. In some embodiments, the hollow portion extends from the top of the cap body to an orifice at the base of the cap body. To form a chamber, the top of the cavity may be closed by fastening a cover onto the cap body. The cover may be constructed of the same piece as the cap body. The cover may incorporate a vent hole 26 or may further incorporate art affixed microbe barrier, filter or a material that expands to close off the vent hole when exposed to a liquid or specific temperature. The bottom of the chamber may be left open or closed by a breakable septum or valve. The hollow chamber may further incorporate a flexible membrane or septum 24. This flexible septum could be manufactured using dip molding, liquid injection silicone molding, blow molding, and/or other methods suitable for the creation of thin elastomeric structures. The flexible septum can be inserted into the cap body cavity 22 assembly sous to effectively isolate the interior portion of the tube from the exterior environment after the cap is in place on the tube. The flexible septum could be designed such that, in the absence of externally applied pressures, its inherent stiffness ensures it is in a preferred, known state of deformation. As a further embodiment, the flexible septum may be replaced by a plunger. In an exemplary embodiment, a cap body approximately 30 mm high by 14 mm diameter may be injection molded of a suitable thermoplastic and contain an interior cavity having at least 500 uL of available volume. The chamber in the cap body could be adapted for useful purposes such as holding or dispensing a reagent, serving as a reservoir to hold waste fluids, serving as a retraction space for an integrated collection tool, or a combination of thereof.

The cap 20 may have an integrated collection tool 30 (FIG. 14B) such as a swab, capillary tube, liquid dropper, inoculation loop, syringe, absorbent pad, forceps, scoop or stick to facilitate the collection of liquid and solid samples and their insertion into the tubule. The collection tool may be designed to collect and deposit a predetermined amount of material into the tube. Reagents may be stored on the collection tool itself. For example, the collection tool may include a swab impregnated with a dry salt such that when the swab is hydrated it would suspend the salt off the swab into solution. Furthermore, the collection tool and cap may be designed such that the collection tool portion retracts into the cap body after depositing the sample into the tubule to leave the tubule segments substantially unencumbered.

The chamber 22 in the cap 20 may be fashioned to store a reagent. To accomplish this, for example, the base of the chamber may be dosed by a breakable septum or valve (not shown) such that when the cap is squeezed, the septum breaks to release the reagent. Such a feature would be useful, for example, if the cap were integrally formed with a collection tool such as a swab or stick. In this instance, the reagent released from the cap chamber could be used to wash a sample off the collection tool into a tube segment or to lyse the sample contained on the collection tool. Reagents may also be released from the cap chamber by opening the breakable septum using pressure generated by compressing a flexible tube segment to force fluid from the tube up into the cap chamber. The chamber in the cap may be fashioned to store waste fluids derived from processing within the tubule. In another embodiment, the base of the chamber may be left open such that when connected to the first opening of the flexible tubule a fluid passage is formed between the tubule and the chamber. As fluid is moved into the cap chamber, the flexible septum 24 contained within can move from an initial position upward so as to accommodate the influx of new fluid. This septum movement can be facilitated by the incorporation of a vent hole 26 on the cap body cover.

Referring to FIG. 13B, after fluid has been transferred into the cap chamber a clamp 310 or actuator 312 in the analyzer can act to compress the tubule and effectively seal off the cap chamber volume from the tubule segments. As an alternative embodiment, the cap chamber may incorporate a pressure gate or check valve (not shown) to prohibit fluid flow from the cap chamber back into the tube segments. As a further alternative, the flexible septum may be omitted with the cap chamber cover including a microbe barrier to permit the free escape of contained gasses but retain all the liquid volumes and infectious agents in the tube. As a further alternative, the flexible septum can be replaced with a plunger that would move axially upward to accommodate additional fluid volumes transferred from the tube segments to the cap chamber. Other methods to accommodate fluidic waste within the cap chamber can be readily envisioned without departing from the scope of the present disclosure.

A substantially rigid frame 50 (FIG. 13A) may be provided to hold the flexible tubule 10 suitably taut by constraining at least the proximal and distal ends of the tubule. In an exemplary embodiment, a first constraint may be provided to permanently attach and seal the tubule to the frame around the first opening of the tube. This seal may be created by welding the flexible tubule to the frame using thermal and/or ultrasonic sources. Alternatively, the seal may be created using a hot-melt adhesive joint with ethylene vinyl acetate, or by making a joint using a UV cure epoxy or other adhesives. In further embodiments, the tubule may be mechanically sealed or insert-molded with the frame. A second constraint may be provided to attach and seal the tubule to the base of the frame. In an exemplary embodiment of this second constraint, this end of the tubule may be sealed flat and attached to the rigid frame by thermal and/or ultrasonic welding techniques. Alternatively, this joint and seal may also be formed using adhesive or mechanical approaches. In an alternative embodiment, the second seal may be similar to the first seal, being substantially open to enable access to the contents of the flexible tubule from the second opening. The tubule and frame materials can be optimized for joint manufacture. For example, the frame can be made of polypropylene having a lower melting point than the thinner tubule to ensure more uniform melting across one or more weld zones. To facilitate welding between the tubule and the frame, the joint area may be tapered or otherwise shaped to include energy directors or other commonly used features enhance weld performance. In an exemplary embodiment, the rigid frame can be made of any suitable plastic by injection molding with its dimensions being approximately 150 mm tall by 25 mm wide.

The rigid frame 50 can incorporate several features to facilitate the compression and flattening of the flexible tubule. For example, in an exemplary embodiment, the flexible tubule 10 may be constrained only at its two axial extremities to allow maximum radial freedom to avoid encumbering the tubule's radial movement as it is compressed. In another embodiment, compression may be facilitated by including a relief area in the frame, near the first opening of the tube. This relief area may be used to facilitate the flexible tubule's transition from a substantially compressed shape in the tubule segments to a substantially open shape at the first opening. Other useful features of the rigid frame that can facilitate flexible tubule compression may include an integral tubule tensioning mechanism. In an exemplary embodiment, this tension mechanism could be manufactured by molding features such as cantilever or leaf type springs directly into the rigid frame to pull the tubule taut at one of its attachment points with the frame.

The rigid frame 50 can facilitate tube identification, handling, sample loading and interfacing to the tube cap. For example, the frame can provide additional area to identify the tube through labels or writing 80 affixed thereto. The plastic materials of the frame may be color coded with the cap materials to help identify the apparatus and its function. The frame may incorporate special features such as changes in thickness or keys to guide its orientation into a receiving instrument or during manufacture. The frame may interface to a sleeve 90 or packaging that covers or protects the flexible tubule from accidental handling, damage, light exposure, and/or heat exposure. The body of the rigid frame may also provide a convenient structure to hold the tube. The frame may have an integral collection tool 32 such as a deflector or scoop to facilitate sample collection into the apparatus. The sample-receiving, end of the frame may also incorporate a tapered or funneled interior surface to guide collected sample into the flexible tube.

In some embodiments, a method of extracting nucleic acids from biological samples by using the apparatus described in the previous paragraphs is contemplated. In certain embodiments, the sequence of events in such a test may include: 1) a biological sample can be collected with a collection tool, 2) the collected sample can be placed into a flexible tubule, which can include a plurality of segments that may contain the reagents required during the test, through a first opening in the tubule, 3) at least one substrate may be set at a controlled temperature and/or other conditions to capture target organisms or nucleic acids during a set incubation period, 4) organisms or molecules, in the unprocessed sample, that may not bind to the substrate can thus be removed by transferring liquid to a waste reservoir, 5) waste may be stored in a waste reservoir, that can be segregated from the target by a clamp and/or actuator compressed against the tubule, 6) a wash buffer, released from another segment of the tubule, may be added to remove reaction inhibitors, 7) an elution reagent, from another segment, may be added to release the target bound to the substrate after incubation at a controlled temperature, and 8) nucleic acids can be detected by techniques well known to those familiar in the art or collected through a second opening in the tubule. In exemplary embodiments the flow of the sample may be from the first opening towards the distal end of the tubule as the test progresses while the flow of waste may be towards the closed sample input opening of the tubule, where a waste chamber in the cap of the tubule receives the waste for storage. Consequently, undesirable contact between a processed sample and surfaces in a reaction vessel that have been touched by the unprocessed sample is avoided, thereby preventing reaction inhibition due to trace amounts of reaction inhibitors present in the unprocessed sample and that might coat the walls of the reaction vessel.

Some embodiments may incorporate the use of a test tube 1 (FIGS. 13A-B), with a flexible tubule 10 divided into a plurality of segments, such as segments 16, 110, 120, 130, 140, 150, 160, 170, 180, and/or 190, that maybe transverse to the longitudinal axis of the tubule, and which may contain reagents, such as reagents 210, 221, 222, 230, 240, 250, 260, 270, 280, 15 and/or 290; as well as an analyzer, that may have a plurality of actuators, such as actuators 312, 322, 332, 342, 352, 362, 372, 382, and/or 392, clamps; such as clamps 310, 320, 330, 340, 350, 360, 370, 380, and/or 390, and blocks, for example 314, 344, and/or 394 (others unnumbered for simplicity); opposing the actuators and clamps, to process a sample. Various combinations of these actuators, clamps, and/or blocks may be used to effectively clamp the tubule closed thereby segregating fluid. In exemplary embodiments, at least one of the actuators or blocks may have a thermal control element to control the temperature of a tubule segment for sample processing. The sample processing apparatus can further have at least one magnetic field source 430 capable of applying a magnetic field to a segment. The sample processing apparatus can further have a detection device 492, such as photometer or a CCD, to monitor a reaction taking place or completed within the tubule.

The combined Use of the tube and the analyzer can enable many sample processing operations. Collecting a sample, such as blood, saliva, serum, soil, tissue biopsy, stool or other solid or liquid samples, can be accomplished by using a sample collection tool 30 that may be incorporated into the cap 20, or features 32 on the tube frame 50. After a suitable amount of the sample has been collected, the cap can be placed onto the first opening of the tube to close the tube and deposit the sample into the first segment. Following this step, the sample contained on the collection tool may be washed off or resuspended with reagents contained in separate chambers within the cap by compressing a portion of the cap. The tube can then be loaded into the, analyzer for further processing. Identification features, such as a barcode or an RF tag, can be present on the tube to designate the sample's identity in a format that can be read by the analyzer and/or a user.

Opening a breakable seal of a tubule segment can be accomplished by applying pressure to the flexible tubule to irreversibly separate the bound surfaces of the tubule wall. An actuator can be used to apply the required pressure to compress a tubule segments containing fluid to open a breakable seal. In embodiments where a segment is delimited by two breakable seals, A and B, the analyzer may preferentially break seal A by physically protecting the seal B region with an actuator or clamp to prevent seal B from breaking while pressure is applied to the segment to break seal A. Alternatively, seal A may be preferentially opened by applying pressure to the segment adjacent to seal A in a precise manner such that; seal A is first opened by the pressure created in the adjacent segment; after seal A is broken, the pressure between the two segments drops substantially due to the additional, combined, segment volume; the reduced pressure in the combined segment is insufficient to break seal B. This method can be used to open breakable seals one at a time without using a protecting, actuator and/or clamp. As a further alternative, the adherence of seal A may be inferior to that of seal B such that seal A can break at a lower pressure than seal B.

A process of moving fluid from one segment to another segment may include, for example, releasing a clamp on one end of the first segment, compressing a clamp on the other end of the first segment, releasing an actuator on the second segment, and compressing an actuator on the first segment to move the liquid from the first segment to the second segment. Alternatively, the damp may be omitted or be opened after releasing the actuator on the second segment A process of mixing two substances, where at least one is liquid, located in adjacent segments may be accomplished by: releasing the clamp between the two segments, moving the liquid contained in the first segment, through an opened breakable seal to the second segment; and alternatively compressing the second segment and the first segment to flow the liquid between the segments.

An agitation can be performed by alternatively compressing and decompressing a tubule segment with an actuator, while both clamps that flank the actuator are compressing the tubule. In another embodiment, agitation can be achieved by alternatively moving liquid between al least two segments.

In embodiments where a tubule segment may contain a liquid having a volume exceeding the volume required for a protocol, a process of adjusting the volume of the liquid in the segment can be executed by: compressing the tubule segment to reduce the gap of between the tube walls to set the volume of the segment to a desired level and allowing the exceeding liquid to flow to the adjacent segment, past a clamp at the end of the segment or adjacent actuator; closing the tubule segment with the clamp or actuator, resulting in an adjusted volume of liquid remaining in the segment.

A process of removing air bubbles may include agitating a segment containing the bubbly liquid. Another process of removing air bubbles may include agitating a first segment containing liquid while closing a second segment; opening the second segment and moving the liquid from the first segment to the second segment; agitating the second segment and adjusting a position of the second actuator to move the liquid-air interface near or above the upper end of the second segment, then clamping the upper end of the second segment to form a fully liquid-infused segment without air bubbles.

A dilution process can be conducted by using the liquid movement process wherein one of the segments includes a diluent and the other includes a substance to be diluted.

A process of reconstituting a reagent from dry and liquid components separately stored in different tubule segments or sub-segments may include compressing the tubule segment or sub-segment containing the liquid components to open the breakable seal connecting to the dry reagent segment, moving the liquid into the dry reagent segment or subsegment, and mixing the dry reagent and liquid components using the mixing process.

Filtration can be performed by using a filter 206 (FIG. 16A) positioned between two segments or two sub-segments. For example, a whole blood sample can be deposited into a first segment with a filter bag. A pore size of the filter can be selected for blood cell filtration. A clamp 300 can then close the end of the segment opposite to the filter bag, and an actuator 302 can compress the first segment to generate pressure to drive plasma flow through the filter into a second segment. In another embodiment, a coagulation, aggregation or agglutination reagent, such as antibody 204 against red cell 202 surface antigens, a red cell coagulate, can be used to induce red cell-red cell binding to form clusters prior to the filtration. The pore size of the filter can be selected to block the clusters while allowing non-aggregated cells to flow through. Applying pressure on the first segment containing red cell clusters and blood can enrich the white cells 208 in the second segment.

Figure 19B:
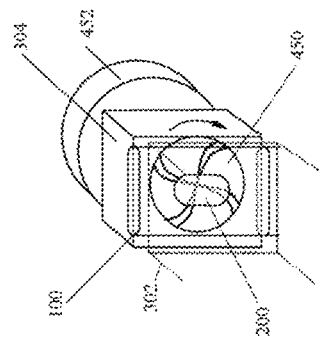
Figure 20:
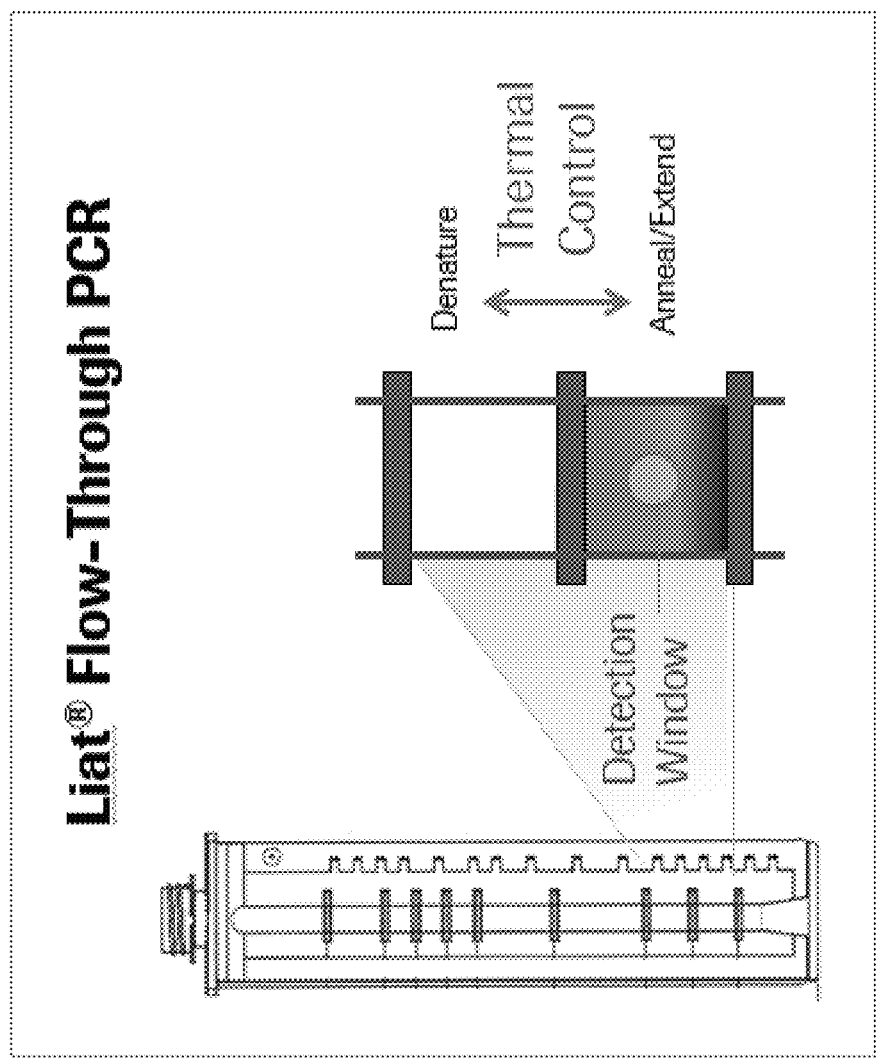
FIG. 20 is a cross sectional view of an exemplary tubule, showing the segments used for PCR. Thermal cycling is accomplished by shuttling the reaction mixture back and forth between two thermal zones, but fluorescence detection is only accomplished in the lower thermal zone where the detection optics are available.

In some embodiments, a grinding process can be conducted by using an actuator to alternately compress and decompress a tubule segment having a toughened wall with a micro-teeth-like inner surface 109 (FIGS. 19A-B), and thus break-up a solid sample, such as biopsy tissue sample, within the tubule segment. In another embodiment, small glass beads can be used with the solid sample to improve the performance of grinding. In a further embodiment, a grinding wheel 450 driven by a motor 452 can be used to form a rotational grinding onto the sample in the tubule segment and drive the movement of glass beads and a biological sample 200 to improve grinding performance. The temperature of a liquid reactant in the segment can be selected so as to improve the grinding result.

Incubation of the contents in a segment can be achieved by setting the corresponding actuator and/or block temperature and applying pressure to the segment to ensure a sufficient surface contact between the tubule wall of the segment and the actuator and the block, and bring the contents of the tubule segment to substantially the same temperature as the surrounding actuator and/or block temperature. The incubation can be conducted in all processing conditions as long as the temperatures of all involved segments are set as required.

Rapid temperature ramping for incubation can be achieved by incubating a fluid in a first segment at a first temperature and setting a second temperature for a second segment adjoining the first segment, after incubation at the first temperature is finished, liquid is rapidly moved from the first segment to the second segment and incubated at the second temperature:

A flow driving through a flow-channel process can be performed by compressing the tubule with a centrally-positioned actuator, and its flanking clamps if any, to form a thin-layer flow channel with a gap of about 1 to about 500 p.m, preferably about 5 to about 500 p.m through segment. The adjacent actuators compress gently on the adjacent segments in liquid communication with the flow-channel to generate an offset inner pressure to ensure a substantially uniform gap of the thin-layer flow channel. The two flanking actuators can then alternatively compress and release pressure on the tubule on their respective segments to generate flow at controlled flow rate. Optional flow, pressure, and/or force sensors may be incorporated to enable closed-loop control of the flow behavior. The flow-channel process can be used in washing, enhancing the substrate binding efficiency, and detection.

A magnetic bead immobilization and re-suspension process can be used to separate the beads from the sample liquid. The magnetic field generated by a magnetic source 430 (FIG. 13B) may be applied to a segment 130 containing a magnetic bead suspension 230 to capture and immobilize the beads to the tube wall. An agitation process can be used during the capturing process. In another embodiment, a flow-channel can be formed on the segment with the applied magnetic field, and magnetic beads can be captured under flow to increase the capturing efficiency. For re-suspending immobilized beads, the magnetic field may be turned off or removed, and an agitation or flow-channel process can be used for resuspension.

A washing process to remove residual debris and reaction inhibitors from a substrate may be conducted by using three basic steps: First an actuator can compress a segment containing the substrate, such as immobilized beads or a sheet, to substantially remove the liquid from this segment. Second, a washing buffer may be moved to the segment by using a process similar to that of reconstituting a reagent from dry and liquid components. For bead-based substrates, a bead re-suspension process can be used followed by bead re-capture on the tubule wall. Third, after a mixing or agitation process, the actuator can compress the segment to remove the used wash liquid from the segment. In another embodiment, a flow-channel can be formed in the segment containing a substrate, which may be either immobilized beads or a sheet A unidirectional flow wash, having laminar characteristics, is generated through the flow channel with the substrate. Finally, all the actuators and clamps, if any, can be closed to remove substantially all the liquid from the segments. In a further embodiment, a combination of the dilution based washing and the laminar flow based washing can be used to further enhance the washing efficiency.

Lysis can be achieved by heating a sample at a set temperature or by using a combination of heat and chemical agents to break open cell membranes, cell walls or uncoated virus particles. In another embodiment, lysis can be achieved using a chemical reagent, such as proteinase K, and a chaotropic salt solution. The chemical reagents can be stored in one of more tubule segments and combined with the sample using the processes disclosed above. In some embodiments, multiple processes such as chemical cell lysis, mechanical grinding and heating, can be combined to break up solid sample, for example tissue collected from biopsy, to maximize the performance.

Capturing target micro-organisms can be achieved by using a substrate. In an embodiment, the surface of the substrate may be coated with at least one binding reagent, such as an antibody, ligand or receptor against an antigen, receptor or ligand on the surface of the target organism (ASA), a nucleic acid (NA), a peptide nucleic acid (PNA) and phosphothioate (PT) nucleic acid probe to capture a specific nucleic acid target sequence complementary to the probe or a target organism. In another embodiment, the surface may be selected to have, or coated to form, an electrostatically charged (EC) surface, such as silica- or ion exchange resin-coated surface, to reversibly capture substantially only nucleic acids. In some embodiments, the substrate may be pre-packed in a tubule segment or subsegment in dry format, and a liquid binding buffer may be packed in another segment. The substrate and the buffer can be reconstituted by using the aforementioned processes.

In some embodiments, a reagent from an adjoining segment can be used to dilute the sample before incubation with the substrate. In some embodiments, the target organisms can be captured to the substrate prior to lysing the microorganisms; while in other embodiments, a lysis step can be conducted before the target capturing step. In preferred embodiments, incubation of the substrate in agitation can be conducted at a desired temperature, for example, at 4° C. for live bacterial capture, or room temperature for viral capture. Capture can be followed by a washing process to remove the residues and unwanted components of the sample from the tubule segment.

In some embodiments, magnetic beads can be used as the substrate for capturing target, and a magnetic bead immobilization and re-suspension process may be used to separate the beads from the sample liquid. In other embodiments where the substrate may be a pad 30 or a sheet 214 (FIGS. 17A-B), the substrate 30 and 214 may be incorporated into the collection tool 36 and/or may be adhered on the tubule wall in a segment.

Elution can be achieved by heating and/or incubating the substrate in a solution in a tubule segment at an elevated temperature. Preferred temperatures for elution are from 50° C. to 95° C. In another embodiment, elution may be achieved by changing the pH of the solution in which the substrate is suspended or embedded. For example, in an exemplary embodiment the pH of the wash solution can be between 4 and 5.5 while that of the elution buffer can be between 8 and 9.

A spore germination process can be conducted by mixing a sample containing bacterial spores with germination solution, and incubating the mixture at a suitable condition. The germinant solution may contain at least one of L-alanine, inosine, Lphenylalanine, and/or L-proline as well as some rich growth media to allow for partial growth of the pre-vegetative cells released from the spores. Preferred incubation temperatures for germination range from 20° C. to 37° C. By coating the substrate with an anti-spore antibody, vegetative cells can be selectively enriched from a sample that contains both live and/or dead spores. The live spores can release a plurality of vegetative cells from the substrate, which can be further processed to detect nucleic acid sequences characteristic of the bacterial species. In some embodiments, the germinant solution can be absorbed in a pad.

In certain embodiments, nucleic acids extracted from the biological samples may be further processed by amplifying the nucleic acids using at least one method from the group consisting of: polymerase chain reaction (PCR), rolling circle amplification (RCA), ligase chain reaction (LCR), transcription mediated amplification (TMA), nucleic acid sequence based amplification (NASBA), and strand displacement amplification reaction (SDA). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or Ampligase™ and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art. In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TaqMan™, molecular beacons™, fluorescence resonance energy transfer (FRET) probes, Scorpion™ probes) and generally use fluorescence quenching as well as the release of quenching or fluorescence energy transfer from one reporter to another to detect the synthesis or presence of specific nucleic acids.

A real-time detection of a signal from a tubule segment can be achieved by using a sensor 492 (FIG. 13B), such as a photometer, a spectrometer, a CCD, connected to a block, such as block 490. In exemplary embodiments, pressure can be applied by an actuator 392 on the tubule segment 190 to suitably define the tubule segment's shape. The format of signal can be an intensity of a light at certain wavelength, such as a fluorescent light, a spectrum, and/or an image, such as image of cells or manmade elements such as quantum dots. For fluorescence detection, an excitation of light from the optical system can be used to illuminate a reaction, and emission light can be detected by the photometer. To detect a plurality of signals having specific wavelengths, different wavelength signals can be detected in series or parallel by dedicated detection channels or a spectrometer.

The disclosed devices and methods can be widely applied in the practice of medicine, agriculture and environmental monitoring as well as many other biological sample testing applications. Nucleic acids isolated from tissue biopsy samples that surround tumors removed by a surgeon can be used to detect pre-cancerous tissues. In these applications, hot-spot mutations in tumor suppressor genes and proto-oncogenes can be detected using genotyping techniques well known to those familiar with the art. Precancerous tissues often have somatic mutations which can readily be identified by comparing the outcome of the genotyping test with the biopsy sample to the patient's genotype using whole blood as a source of nucleic acids. Nucleic acids isolated from white blood can be used to detect genetic variants and germline mutations using genotyping techniques well known to those familiar with the art. Examples of such mutations are the approximately 25 known mutants of the CFTR gene recommended for prenatal diagnosis by the American College of Medical Genetics and the American College of Obstetricians and Gynecologists. Examples of genetic variants are high frequency alleles in glucose-6-phosphate dehydrogenase that influence sensitivity to therapeutic agents, like the antimalarial drug Primaquine.

Another example of genetic variations with clinical relevance are alleles pertaining to increased risks of pathological conditions, like the Factor V Leiden allele and the increased risk of venous thrombosis. Nucleic acids isolated from bacteria can be used to detect gene coding sequences to evaluate the pathogenicity of a bacterial strain. Examples of such genes are the Lethal Factor, the Protective Antigen A, and the Edema factor genes on the PXO1 plasmid of *Bacillus anthracis* and the Capsular antigen A, B, and Con the PXO2 plasmid of *B. anthracis*. The presence of these sequences allows researchers to distinguish between *B. anthracis* and harmless soil bacteria. Nucleic acids isolated from RNA viruses can be used to detect gene coding sequences to detect the presence or absence of a virus or to quantify a virus in order to guide therapeutic treatment of infected individuals.

A particularly significant utility of such assays is the detection of the human immunodeficiency virus (HIV), to guide anti-retroviral therapy. Nucleic acids isolated from DNA viruses can be used detect gene coding sequences to detect the presence or absence of a virus in blood prior to their use in the manufacturing of blood derived products. The detection of hepatitis B virus in pools of blood samples is a well-known example of this utility to those familiar in the art. The presence of verotoxin *Escherichia coli* in ground beef is a good example of the potential agricultural uses of the apparatus. Detecting the Norwalk virus on surfaces is an example of a public health environmental monitoring application.

Some embodiments may incorporate the use of a test tube 1, with a flexible device 10 divided into a plurality of segments, such as segments 16, 110, 120, 130, 140, 150, 160, 170, 180, and/or 190, that may be transverse to the longitudinal axis of the device, and which may contain reagents, such as reagents 210, 221, 222, 230, 240, 250, 260, 270, 280, and/or 290; as well as an analyzer, that may have a plurality of compression members, such as actuators 312, 322, 332, 342, 352, 362, 372, 382, and/or 392, clamps, such as clamps 310, 320, 330, 340, 350, 360, 370, 380, and/or 390, and blocks, for example 314, 344, and/or 394 (others unnumbered for simplicity); opposing the actuators and clamps, to process a sample. Various combinations of these actuators, clamps, and/or blocks may be used to effectively clamp the device closed thereby segregating fluid. In exemplary embodiments, at least one of the actuators or blocks may have a thermal control element to control the temperature of a device segment for sample processing. The sample processing apparatus can further have at least one magnetic field source 430 capable of applying a magnetic field to a segment. The sample processing apparatus can further have a detection device 492, such as photometer or a CCD, to monitor a reaction taking place or completed within the device.

Fluid can be driven through a flow-channel by compressing the device with a centrally-positioned actuator, and its flanking clamps if any, to form a flow channel with a gap of about 1 to about 500 um, preferably about 5 to about 500 um through each segment. The adjacent actuators gently compress the adjacent segments in liquid communication with the flow-channel to generate an offset inner pressure to ensure a substantially uniform gap of the flow channel. The two flanking actuators can then alternatively compress and release pressure on the device on their respective segments to generate flow at a controlled flow rate. Optional flow, pressure, and/or force sensors may be incorporated to enable dosed-loop control of the flow behavior. The flow-channel process can be used in washing, enhancing the substrate binding efficiency, and detection.

A particle immobilization and re-suspension process can be used to separate the particles from the sample liquid. The magnetic field generated by a magnetic source 430 (FIG. 1) may be applied to a segment containing a magnetic particle suspension to capture and immobilize the particles to the tube wall. An agitation process can be used during the capturing process. In another embodiment, a flow-channel can be formed in the segment with the applied magnetic field, and magnetic particles can be captured in the flow to increase the capturing efficiency. To resuspend immobilized particles, the magnetic field may be turned off or removed, and an agitation or flow-channel process can be used for re-suspension.

Embodiments of the present invention will be further described in the following examples, which do not limit the scope of the invention described in the claims.

EXAMPLES

Example 1 Verification of Quenching by a Quenching Oligonucleotide

An experiment was performed to verify that a quenching oligonucleotide containing a quencher moiety would be able to hybridize with the fluorescently-labeled tag portion of an oligonucleotide probe and quench the fluorescent signal at a temperature below the melting temperature of the duplex but not at a temperature above the melting temperature in which the duplex has been dissociated. Table 2 contains the nucleotide sequences of the tag portion and the quenching oligonucleotide. Quenching oligonucleotide Q0 does not contain the quencher, whereas quenching oligonucleotide Q1, otherwise identical in sequence to Q0, also contains a BHQ-2 quencher at its 5' terminus.

TABLE 2

| Name | Sequence | Modifications | SEQ ID NO: |
|---|---|---|---|
| 9FAM9TAG | CGTCGCCAGTCAGCTCCGG9F9T | 9 = C9 spacer, F = FAM | 1 |
| Q0 | CCGGAGCTGACTGGCGACGp | p = phosphate | 2 |
| Q1 | QCCGGAGCTGACTGGCGACGp | p = phosphate, Q = BHQ-2 | 3 |

The 9FAM9 TAG oligonucleotide was incubated without a quenching oligonucleotide (QX) or with the Q0 or Q1 quenching oligonucleotide at 1:5 molar ratio. The mixtures were then cycled in 50 μL reactions that consisted of 60 mM Tricine, 120 mM potassium acetate, 5.4% DMSO, 0.027% sodium azide, 3% glycerol, 0.02% Tween 20, 43.9 uM EDTA, 0.2 U/uL UNG, 0.1 uM 19TAGC9FAMC9, 0.5 uM Q0 or Q1, 400 μM dATP, 400 μM 4CTP, 400 μM dGTP, 800 μM dUTP, and 3.3 mM manganese acetate. Cycle conditions resembling a typical PCR amplification reaction are shown in Table 3.

TABLE 3

| Step | Description | Cycle # | Temperature (° C.) | Time | Data acquisition |
|---|---|---|---|---|---|
| 1 | Sterilization/RT | 1 | 50 | 2 min | none |
| | | | 94 | 5 sec | none |
| | | | 55 | 2 min | none |
| | | | 60 | 6 min | none |
| | | | 65 | 4 min | none |
| 2 | Dark Cycles (no data acquisition) | 5 | 95 | 5 sec | none |
| | | | 55 | 30 sec | none |
| 3 | TaqMan Cycles | 55 | 91 | 5 sec | none |
| | | | 58 | 25 sec | fluorescence read |
| | | | 80 | 5 sec | fluorescence read |

The results of the experiment are shown in FIG. 6. When the signal from the FAM dye was measured at 58° C., fluorescence was detected with no quenching oligonucleotide (QX) or with a quenching oligonucleotide with no quenching moiety (Q0) but no signal was detected at any of the cycles in the presence of the Q1 quenching oligonucleotide. In contrast, when fluorescence was measured at 80° C., signals could be detected in all cycles even in the presence of the Q1 quenching oligonucleotide, which demonstrates that at the higher temperature, the Q1 quenching oligonucleotide was no longer hybridized with the TAG, and no quenching was observed.

Example 2 Real-Time PCR with TAGS Probe and Quenching Oligonucleotide

A real-time PCR study was conducted using samples that contained various concentrations of an internal control template (GIC) mixed with various concentrations of a template sequence from HIV-1 Group M (HIM). A standard TaqMan® hydrolysis probe (G0) that hybridizes to the GIC sequence and a tagged probe (L24) with a complementary quenching oligonucleotide (Q9) and an annealing portion that hybridizes to the HIM sequence were used to detect the amplification products generated from these two templates. Both probes were labeled with FAM and Table 4 shows their sequences and the sequence of the quenching oligonucleotide.

TABLE 4

| Name | Sequence | Modifications | SEQ ID NO: |
|---|---|---|---|
| G0 | FTGCGCGTCCCGQTTTTGATACTTCF GTAACCGTGCp | F = FAM, Q = BHQ-2, p = phosphate | 4 |
| L24 | QTCTCTAGCAGTGGCGCCCGAACA GGGACF*CACACATTGGCACCGCCGT*Q *CT*p | F = FAM, Q = BHQ-2, p = phosphate tag underlined | 5 |
| Q9 | AGACGGCGGTGCCAATGTGTGQp | Q = BHQ-2, p = phosphate | 6 |

Four concentrations of GIC: 0 copies/reaction (cp/rxn), 100 cp/rxn, 1,000 cp/rxn, and 10,000 cp/rxn were mixed with four concentrations of HIM: 0 cp/rxn, 10 cp/rxn, 100 cp/rxn, and 1,000 cp/rxn to form sixteen different concentration combinations. PCR reagents and cycle conditions were as described in Example 1 and Table 3 with the exception that 100 nM of the G0 and L24 probes and 200 nM of the Q9 quenching oligonucleotide were used in the reactions. Fluorescence readings from the FAM label were taken at 58° C. and at 80° C. for each cycle beginning from cycle #6 (see Table 3).

The results of these experiments are shown in FIGS. 7-9. The fluorescence readings at 58° C. are shown as growth curves in FIG. 7. FIG. 7A shows the growth curves generated with no HIM present and with 0, 100, 1,000 or 10,000 cp/rxn GIC. Interestingly, there are essentially no differences in the fluorescence intensities and the Cycle threshold (Ct) values—in the growth curve readings at 58° C. in the presence of HIM at 10 cp/rxn (FIG. 7B), 100 cp/rxn (FIG. 7C) and 1,000 cp/rxn. (FIG. 7D) which indicate that only the FAM signal from the standard TaqMan® G0 probe is detected at this temperature. This is because the FAM label on the L24 TAGS probe is very efficiently quenched by the quencher on the Q9 quenching oligonucleotide and does not interfere with the detection of the GIC target.

The fluorescence readings at 80° C. are shown as growth curves in FIG. 8. FIG. 8A shows the growth curves generated with no GIC present and with 0, 10, 100 or 1,000 cp/rxn HIM. The fluorescence can now be detected from the FAM label on the L24 probe because it is no longer quenched by both the quencher on the "annealing portion" of the probe (due to hydrolysis by the nuclease) and the quencher on the quenching oligonucleotide (Q9) due to strand dissociation at this high temperature. Although the fluorescence intensity from the L24 probe is considerably lower than that of the G0 probe, it is still sufficient to calculate the Ct values that correspond to the starting concentrations of HIM. However, when HIM and GIC are both present, the fluorescence readings at 80° C. generate complex curves due to the stronger fluorescence that is detected from the G0 probe. (see FIGS. 8B, 8C, 8D). Therefore, in order to "uncover" the fluorescent signal from the L24 TAGS probe, it would be necessary to subtract out the fluorescent signal from the G0 probe, which would involve subtracting the 58° C. fluorescence readings (which is only contributed by the G0 probe) from the 80° C. fluorescence readings and derive growth curves that would resemble those observed in FIG. 8A.

When 100% of the 58° C. fluorescence readings were subtracted from the 80° C. fluorescence readings, the derived growth curves showed negative values which indicated that there was overcompensation of the subtraction. The reason for this observation was due to the reduced fluorescence intensity of the FAM label at 80° C. compared to the intensity at 58° C. Therefore, a "normalization" coefficient was deemed necessary and it was then empirically determined that 84% of the 58° C. signals subtracted from the 80° C. signals generated the best results. The derived growth curves are shown in FIGS. 9A, 9B, 9C and 9D and all are virtually identical to the 0 GIC growth curves of FIG. 8A. These results show that that fluorescent signals that indicate the presence of GIC can be separated from fluorescent signals that indicate the presence of HIM and demonstrate the multiplexing utility of the present invention.

Example 3 Real-Time PCR with Probes Having Different Fluorescent Dyes

Figure 10:
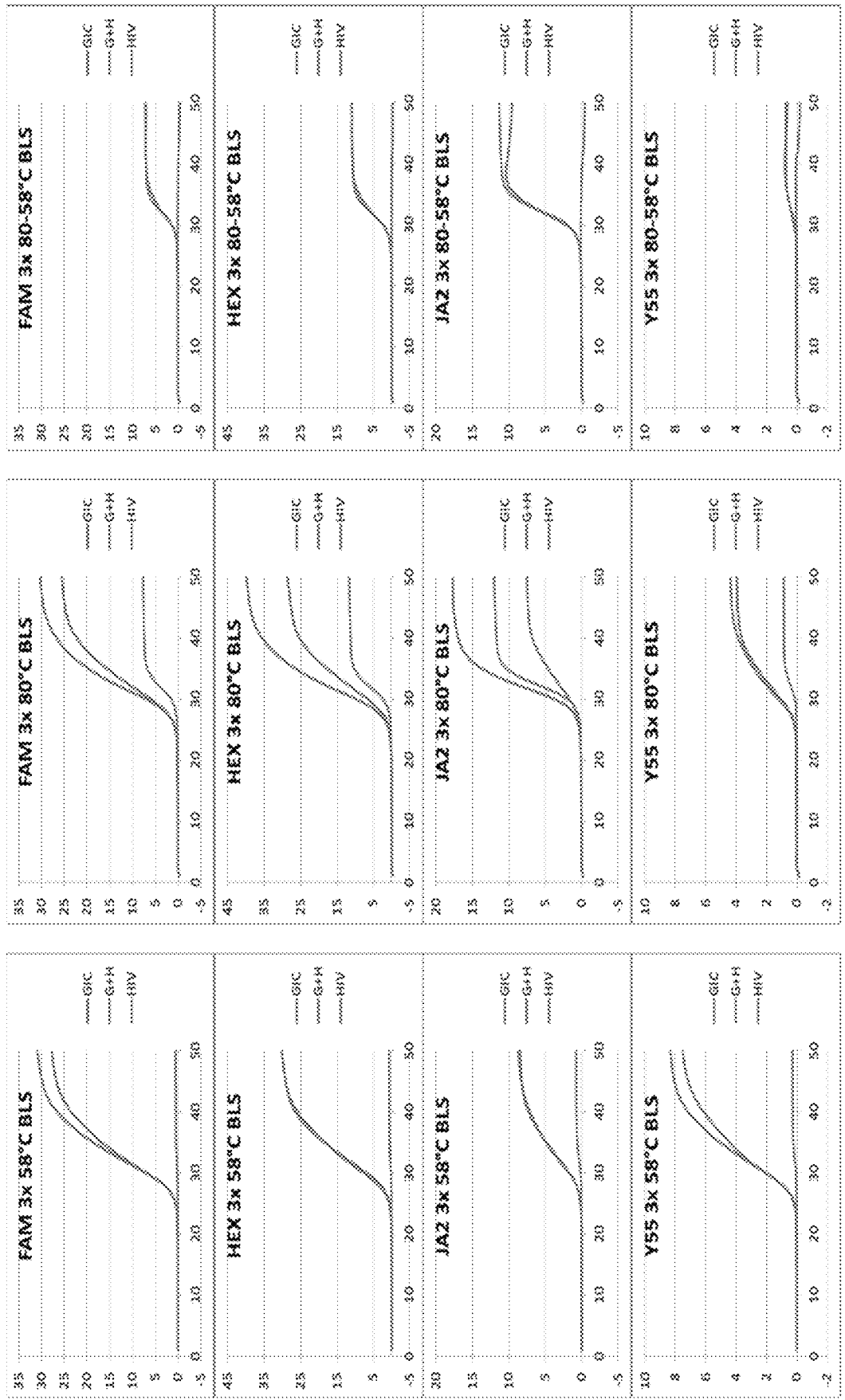
FIG. 10 shows the PCR growth curves generated from an internal control template (GIC) or an HIV template (HIV), or both GIC and HIV templates (G+H) using a standard TaqMan® GIC probe (G0) and a TAGS HIV probe (L24) with complementary quenching oligonucleotide (Q9) in which both probes are labeled with FAM (1st row), with HEX (2nd row), with JA270 dye (3rd row) or with Cy5.5 (4th row).

A series of experiments were performed as described in Example 2 except that the G0 and L24 probes were labeled with FAM dye in the first set, with HEX dye in the second set, with JA270 dye in the third set and with Cy5.5 dye in the fourth set. In each set of experiments, PCR amplification was performed with only GIC template present at 100 cp/rxn, only HIV template present at 1000 cp/rxn or with both GIC (100 cp/rxn) and HIV (1000 cp/rxn) templates present. The results of the experiment are shown in FIG. 10. In fluorescence readings at 58° C. (FIG. 10, $1^{st}$ column), only signals generated by the G0 probes for the GIC templates were observed, as expected, since the L24 probes were still hybridized to the Q9 quenching oligonucleotides. In fluorescence readings at 80° C. (FIG. 10, $2^{nd}$ column), signals generated by both the G0 probes (for GIC) and the "unquenched" L24 probes for HIV) were observed. After using a normalized coefficient for each fluorescent dye, the 58° C. signals subtracted from the 80° C. signals generated the growth curves derived from the HIV template only (FIG. 10, $3^{rd}$ column). The signals generated from HEX and JA270 were similar to or higher than the signals from FAM while the signals from Cy5.5 were considerably lower than FAM signals but nevertheless detectable.

Example 4 Real-Time PCR with L-DNA TAGS Probe and Quenching Oligonucleotide

Figure 11:
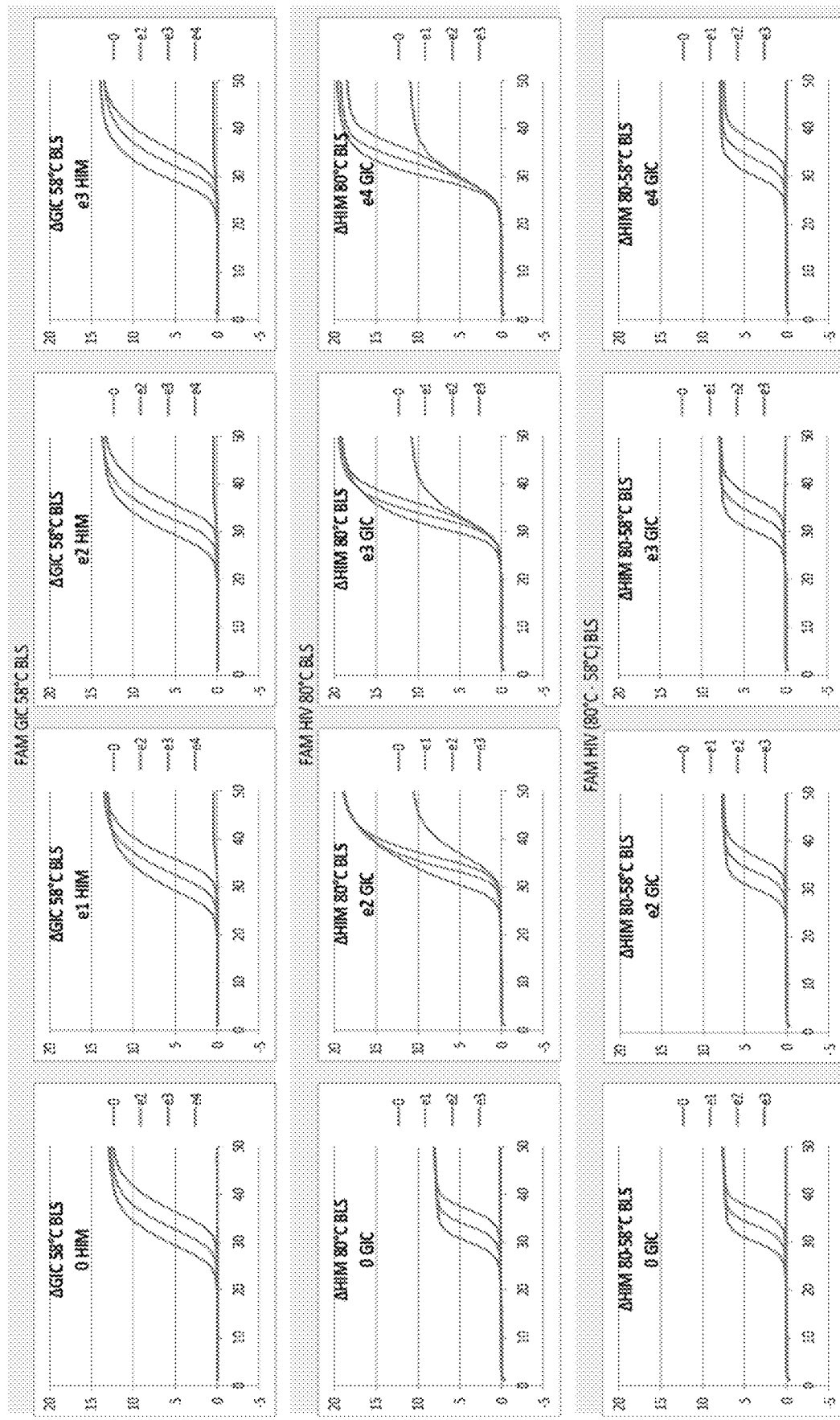
FIG. 11 shows the PCR growth curves of the experiment as described in Example 4 in which the L24 TAGS probe contains L-DNA instead of D-DNA.

An experiment identical to the experiment described in Example 2 was performed with the exception that the L24 tag probe to detect the HIV-1 Group M (HIM) template was comprised entirely of L-deoxyribose nucleotides instead of the "natural" D-deoxyribose nucleotides (denoted "L-L24 probe"). The results of the experiment are shown in FIG. 11 where it was observed that the fluorescence signals generated by using the L-L24 TAGS probe were 4-5 fold higher than the signals generated using the L24 TAGS probe.

Figure 12:
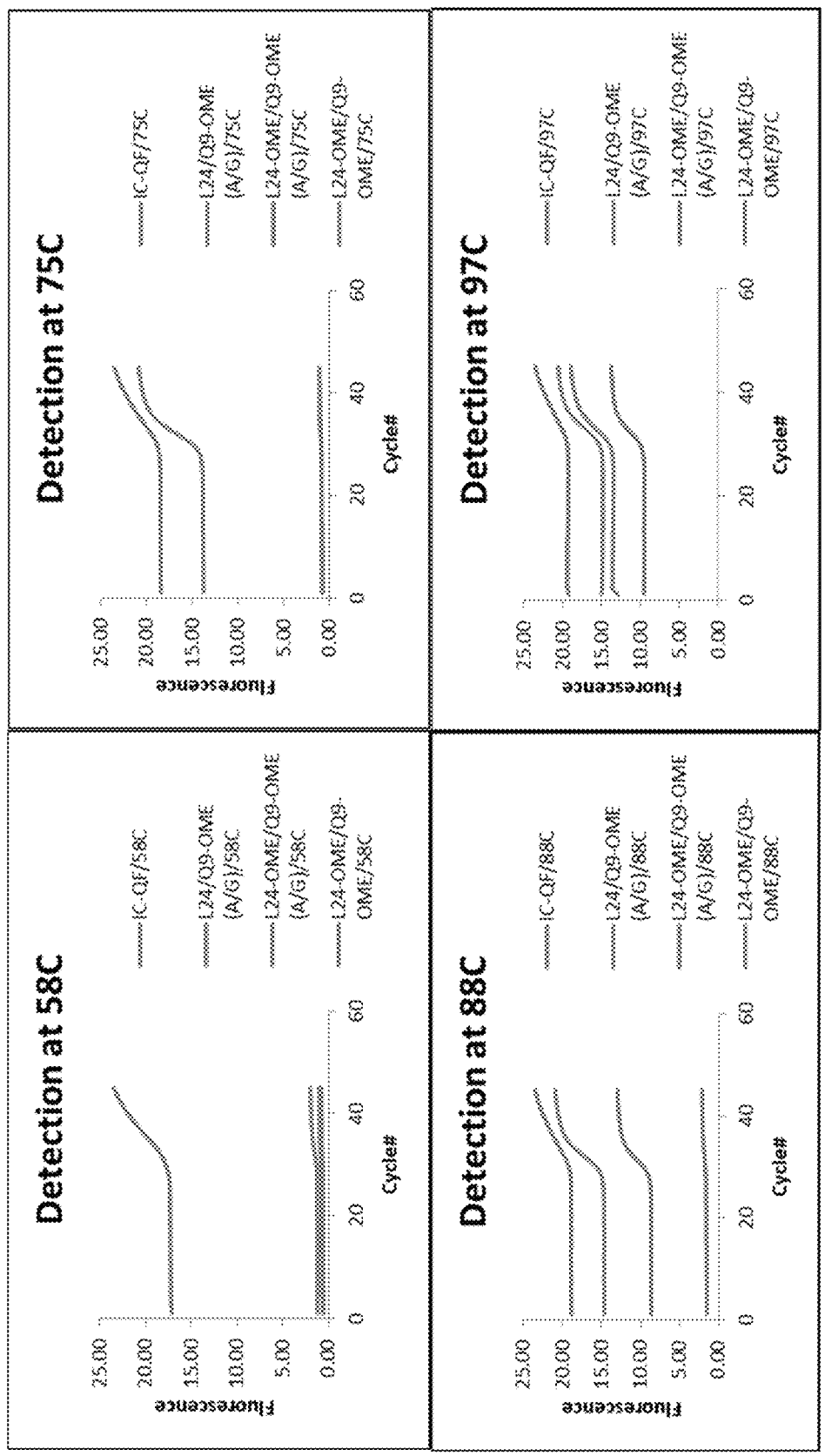
FIG. 12 shows the PCR growth curves of the experiment as described in Example 5 in which fluorescence signal detection was measured at 58° C., 75° C., 88° C. or 97° C. in the presence of a standard TaqMan® GIC probe (IC-QF), a TAGS HIV probe (L24) with a quenching oligonucleotide that has A and G nucleotides modified with 2'-O Me substitutions (Q9-OMe A/G), a TAGS HIV probe that has all nucleotides modified with 2' OMe substitutions (L24-OMe) With a quenching oligonucleotide (Q9-OMe A/G), and a TAGS HIV probe (L24-OMe) with a quenching oligonucleotide that has all nucleotides modified with 2'-OMe substitutions (Q9-OMe).

Example 5 Real-Time PCR with TAGS Probes and Quenching Oligonucleotides Having 2'-O Methyl Modifications An experiment similar to the one described in Example 2 was performed except that TAGS probes and quenching oligonucleotides having nucleotide modifications were used. In addition to the "standard" L24 probe used to detect the presence of the HIM template, the TAGS probe, L24-OME was generated in which every nucleotide in the tag portion of the probe (shown in Table 4 as the underlined portion of L24) was modified by having an O-methyl substituent on the 2' position of the ribose moiety (2'-O Me). Two modified Q9 quenching oligonucleotides for hybridizing to the tag portion of L24 were also generated. Q9-OME had every nucleotide modified by a 2'-OMe substituent, and Q9-OME (A/G) had only the A and G nucleotides modified by a 2'-O Me substituent. Detection of the HIM template was performed using three different combinations of the tag portion and quenching oligonucleotide: L24 with Q9-OME (A/G), L24-OME with Q9-OME (A/G) and L24-OME with Q9-OME. Results of this experiment are shown in FIG. 12.

As expected, at 58° C., only the fluorescent signal from the G0 TaqMan® probe could be detected. At 75° C., fluorescent signals were detected from G0 and from L24/Q9-OME (A/G) but not from the two other tag-quenching oligonucleotide combinations. At 88° C., fluorescent signals could also be detected from L24-OME/Q9-OME (A/G) and at 97° C., signals were detected from all the probes, including the L24-OME/Q9-OME combination. These results show not only that fluorescent readings from three separate temperatures can be achieved using TAGS probes and quenching molecules but that nucleotide modifications such as 2'-OMe can be selectively introduced to the nucleotide sequence of the tag portion or to the quenching oligonucleotide or to both in order to alter the melting temperature of the tag-quenching oligonucleotide duplex without having to change either their sequences or their lengths.

Example 6 Multi-Segment Tubule PCR Analyzer for High Temperature Fluorescence Reading Adapting the TAGS strategy to the cobas® Liat® System poses some unique challenges. In plate-based PCR machines, it is relatively straight forward to execute fluorescence readings at multiple temperatures because the reaction mixture remains stationary, and the temperature is ramped up and down between anneal-extend and denaturation temperatures. In contrast, the temperature cycling in the cobas® Liat® System is achieved by shuttling the reaction mixture back and forth between two thermal zones maintained at the anneal-extend temperature, and at the denaturation temperature. This is an elegant design that allows for very rapid temperature equilibration and consequently rapid PCR cycling. Because of this configuration, the current versions of the cobas® Liat® System hardware have been designed such that fluorescence reading can only occur in the anneal-extend segment. While it is possible to ramp the temperature up and down in the anneal-extend segment, such a process is quite slow, and a PCR reaction designed to be executed in only the anneal-extend segment would take a very long time which is not suitable for point of care applications.

In order to circumvent this problem, a novel strategy has been devised that incorporates a fluorescence reading step of the hot liquid after it is returned the anneal-extend segment from the denaturation segment, but has not yet cooled down to the anneal-extend temperature. In order to accomplish this, new assay scripts have been developed with instructions to collect fluorescence data twice during each PCR cycle, once during the cooling phase and a second time after temperature equilibration in the anneal-extend segment This strategy enables the two-temperature detection goal with minimum impact on the assay time.

Figure 21:
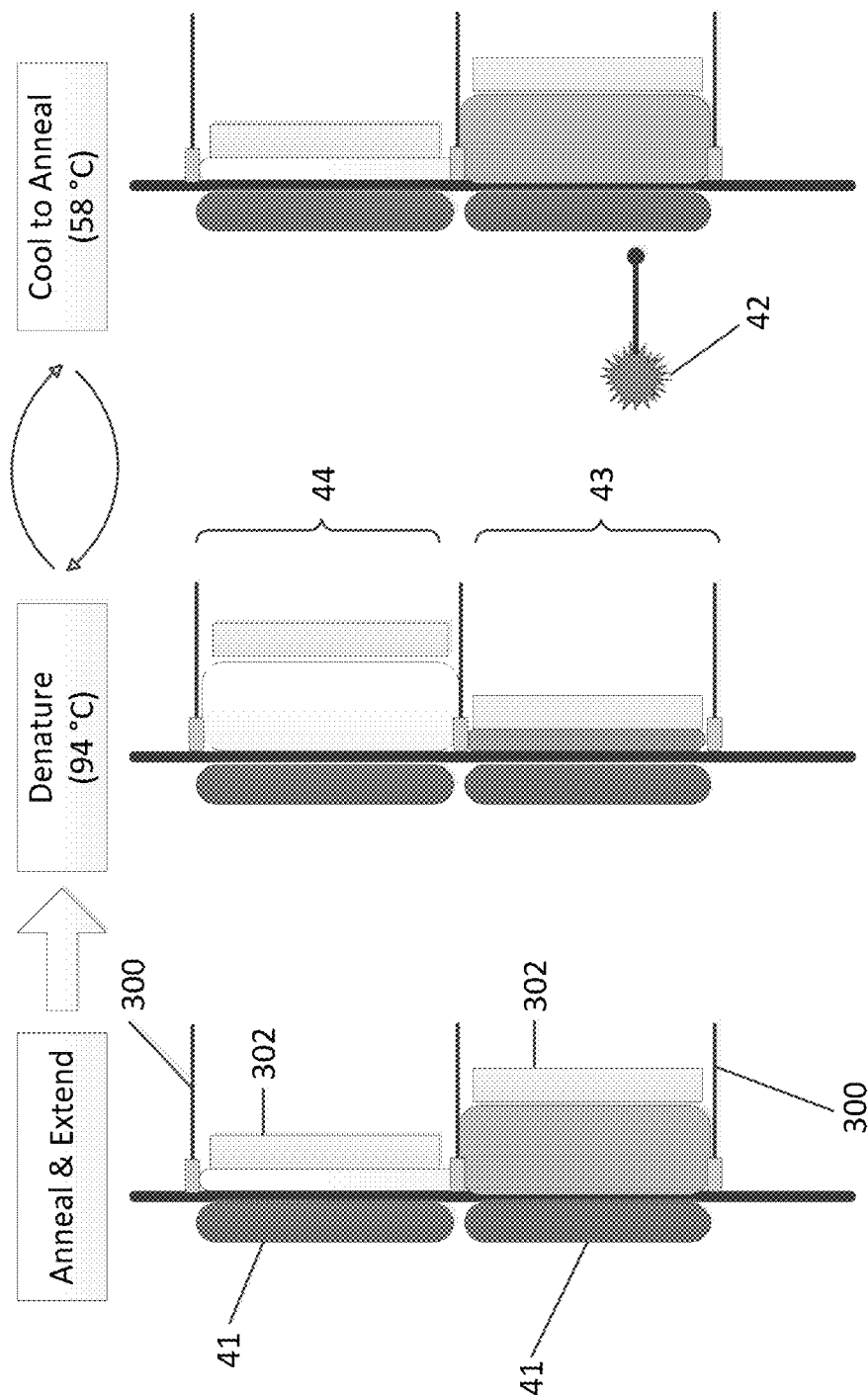
FIG. 21 is a depiction of the strategy employed to read fluorescence at two different temperatures. In addition to the normal fluorescence reading usually obtained after the liquid has equilibrated to the anneal-extend temperature, a second "High Temperature" fluorescence reading is executed before the liquid has cooled down significantly.

As shown in FIG. 21, the thermal cycling is accomplished by shuttling the PCR reaction mixture back and forth between two different segments of the tube, each maintained at a fixed temperature. The PCR reaction mixture is moved among different segments of tube 10 using damps 300 and actuators 302. The denaturation segment 44 is maintained at 94° C., and the anneal-extend segment 43 is maintained at 58° C., each via heating/cooling devices 41. In each cycle, the PCR reagent is moved to anneal-extend segment 43 for the denaturing step, and to denaturation segment 44 for the anneal/extend step. Moving the hot liquid from anneal-extend segment 43 to denaturation segment 44 allows the reagent to cool by passive cooling, but there is a time lag before the reaction mixture equilibrates to 58° C. A first high temperature fluorescence signal is captured at a specified time shortly after the reaction mixture enters anneal-extend segment 43 but before temperature equilibration at 58° C. is achieved, using light source 42. A second fluorescence signal is captured after the temperature is equilibrated at 58° C., and annealing and extending occur in anneal-extend segment 43. The part of the assay script that controls the thermocycling profile is shown in Table 5. Fluorescence readings from the FAM labels were taken at 58° C. and at a high temperature for each cycle beginning from cycle #6.

TABLE 5

| | Setting | | |
|---|---|---|---|
| Steps | Temperature (° C.) | Time (seconds) | Cycle Number |
| RT | 55 | 30 | 1 |
| | 60 | 60 | |
| | 65 | 115 | |
| PCR1 | 95 | 5 | 5 |
| | 55 | 5 | |
| | 58 | 5 | |
| | 60 | 5 | |
| PCR2 | 94 | 4 | 6-40 |
| | 58 | 4 | |
| | 58 | 12 + 0.086/cycle | |

Example 7 Real-Time PCR with TAGS Probe and Quenching Oligonucleotide in the cobas® Liat® Analyzer A real-time PCR study was conducted in a cobas® Liat® system, using samples that contained either 10,000 copies of an internal control template (GIC); 5,000 copies of a template sequence from HIV-1 Group M (HIM); or a mixture of 10,000 copies of GIC and 5,000 copies of HIM. A standard TaqMan® hydrolysis probe (G0) that hybridizes to the GIC sequence and a TAGS probe (L-L24) with a complementary quenching oligonudeotide (L-Q9) and an annealing portion that hybridizes to the HIM sequence were used to detect the amplification products generated from these two templates. The tag portion of the L-L24 TAGS probe and the quenching oligonucleotide (L-Q9) were comprised entirely of L-deoxyribose nucleotides instead of the "natural" D-deoxyribose nucleotides. Both probes (G0 and L-L24) were labeled with FAM.

In addition to the target templates, the final PCR reactions consisted of 1 µM amplification primers, 0.1 µM G0 probe, 0.3 µM L-L24 probe, 0.4 µM L-Q9 quenching oligo, 60 mM Tricine, 120 mM potassium acetate, 5.4% DMSO, 0.027% sodium azide, 3% glycerol, 0.02% Tween 20, 43.9 uM EDTA, 0.2 U/uL UNG, 400 µM dATP, 400 µM 4 CTP, 400 µM dGTP, 800 µM dUTP, and 3.3 mM manganese acetate. The reactions were treated as described above for Example 6.

The results of these experiments are shown in FIGS. 22A through D. In each of the 4 panels, a 58° C. curve, a high temperature curve, and a curve obtained by plotting the difference between the high temperature, and 58° C. fluorescence readings are shown. Growth curves are shown for the HIM target (FIG. 22A), a reaction with both HIM and GIC targets (FIG. 22B), GIC target (FIG. 22C), and the negative control (FIG. 22D). When only the HIM target is present, no growth curve is observed at 58° C. as the cleaved HTV probe is still quenched by the quencher oligonucleotide. However, at the high temperature, a clear fluorescence signal can be seen as the quencher oligonucleotide is no longer hybridized to the cleaved TAGS probe. As expected, a difference plot obtained by subtracting 58° C. fluorescence from the high temperature fluorescence still gives a signal. When only the GIC target is present, the 58° C. fluorescence data shows the expected growth curve due to cleavage of G0 which is a standard TaqMan® probe. Further, the high temperature fluorescence also gives a positive signal, but the difference plot shows no growth curve. When no target is present, no growth curves are observed at either 58° C. or at the high temperature. When both HIM and GIC targets are present, growth curves are seen in in all 3 plots: 58° C. fluorescence, high temperature fluorescence, and high temperature minus 58° C. fluorescence.

Example 8 Template Titration of HIV and GIC Targets in the cobas® Liat® Analyzer This example demonstrates that not only two distinct targets can be simultaneously detected in the same fluorescence channel simultaneously, but the relative ratios of the two targets can also be accurately determined. The experimental conditions were as described in Example 7. Dual targets (HTM and GIC) were added to the reactions by either keeping HIM constant and varying GIC, or keeping GIC constant and varying HIM. The results are shown in FIGS. 23A and 23B.

Figures 23, 23A:
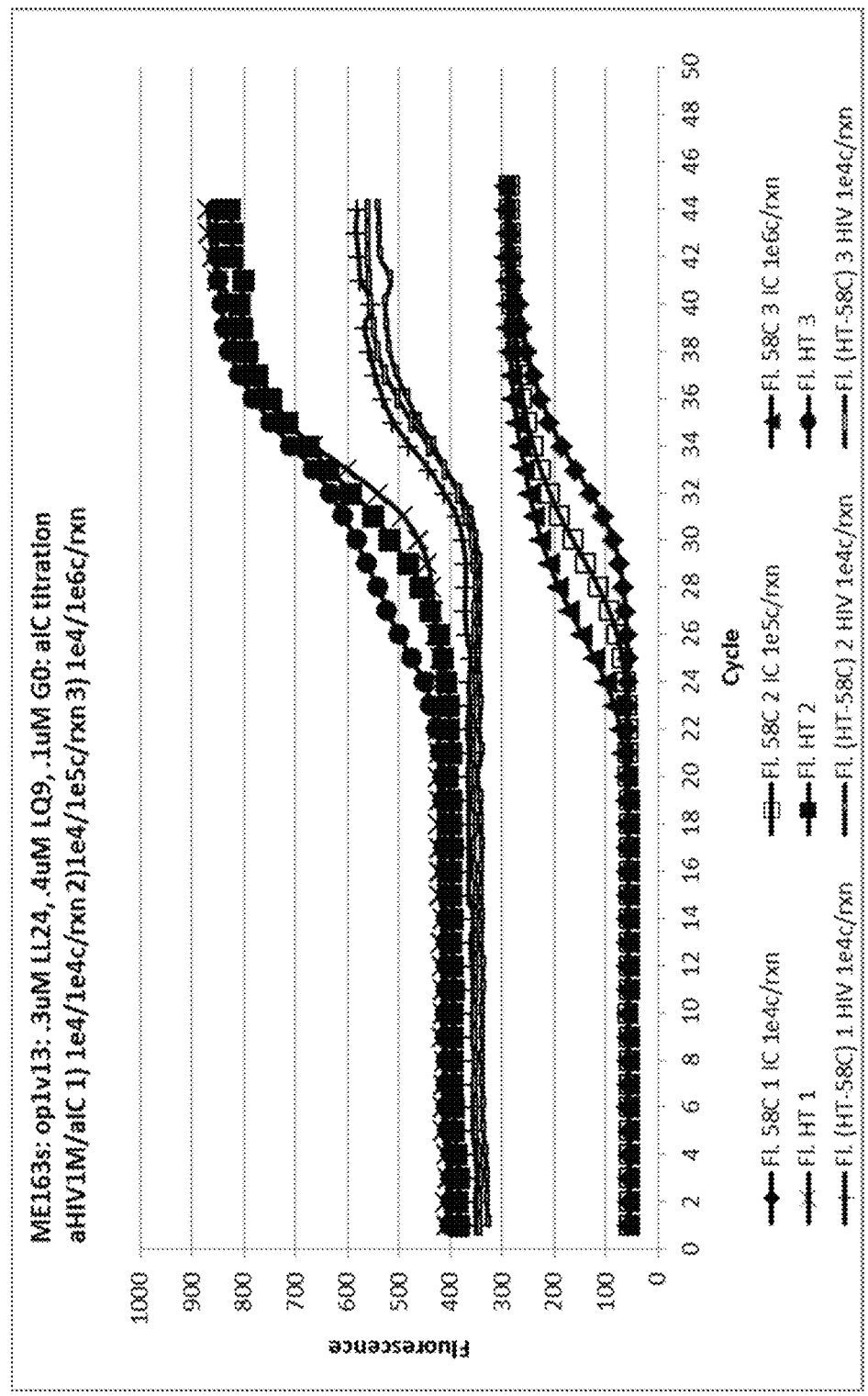
FIG. 23 shows the PCR growth curves generated from combined HIM and GIC targets at different levels, using a Tag Man probe to detect GIC and a TAGS probe to detect HTV.
FIG. 23A shows an overlay of growth curves from reactions with $10^4$ ("e4") copies of HIV, and $10^4$, $10^5$ ("e5"), or $10^6$ ("e6") copies of GIC targets.

In FIG. 23A, the growth curves are overlaid for experiments with $10^4$ HIM+$10^4$ GIC, $10^4$ HIM+$10^5$ GIC, and $10^4$ HIM+$10^6$ GIC copies of target. As expected, the Cts for the GIC target, as seen in the 58° C. growth curves, decrease with increasing levels of GIC. However, it can be seen that the HIM target was the same in all the reactions because the high temperature minus 58° C. fluorescence plots show the same Ct values.

In FIG. 23B, the growth curves are overlaid for experiments with $10^4$ HIM+$10^4$ GIC, $10^5$ HIM+$10^4$ GIC, and $10^6$ HIM+$10^4$ GIC copies of target. As expected, the Cts for the HIM target, as seen in the the high temperature minus 58° C. fluorescence plots growth curves, decrease with increasing levels of HIM. However, it can be seen that the GIC target was the same in all the reactions because the 58° C. fluorescence plots show the same Ct values.

While the foregoing invention has been described in some detail for purposes of clarity and understanding, it will be clear to one skilled in the art from a reading of this disclosure that various changes in form and detail can be made without departing from the true scope of the invention. For example, the methods described above can be used in various combinations. All US patents and patent applications cited herein are hereby incorporated by reference.

---

The invention claimed is:

1. A method for detecting a target nucleic acid in a sample, comprising:
   (a) contacting a sample suspected of containing said target nucleic acid in a reaction vessel with a mixture comprising:
      (i) at least one pair of oligonucleotide primers, each oligonucleotide primer of said pair being capable of hybridizing to opposing strands of a subsequence of said target nucleic acid;
      (ii) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of said target nucleic acid that is bounded by said pair of oligonucleotide primers, said probe further comprising an interactive dual label comprising a reporter moiety located on said tag portion and a first quencher moiety located on said annealing portion, and wherein said reporter moiety is separated from said first quencher moiety by a nuclease susceptible cleavage site; and wherein said tag portion hybridizes to a quenching oligonucleotide that comprises one or more quencher moieties capable of quenching said reporter moiety when said quenching oligonucleotide is hybridized to said tag portion;
   (b) wherein said reaction vessel is a tubule, comprising
      (i) a proximal end having an opening through which a sample is introducible;
      (ii) a distal end; and
      (iii) at least a first segment containing at least one nucleic acid extraction reagent, a second segment distal to the first segment and containing a wash reagent, and a third segment distal to the second segment and containing one or more amplification reagents, each of said segments being:
         (A) defined by the tubule;
         (B) fluidly isolated, at least in part, by a fluid-tight seal formed by a bonding of opposed wall portions of the tubule to one another such that:
            (1) the seal is broken by application of fluid pressure on a segment that is fluidly isolated in part by the seal; and
            (2) the seal is capable of being clamped where the opposed wall portions of the tubule are bonded, without breaking the scat, to prevent the seal from being broken by application of fluid pressure on a segment that is fluidly isolated in part by the seal;

(C) so expandable as to receive a volume of fluid expelled from another segment; and so compressible as to contain substantially no fluid when so compressed;

(iv) a cap for closing the opening, the cap containing a chamber in fluid communication with the tubule, and the cap permitting free escape of gasses but retaining all liquid volumes and infectious agents in the tube;

(v) a rigid frame to which the tubule's proximal and distal ends are held; and (vi) an integral tubule tensioning mechanism or an attachment of the tubule to the frame that pulls the tubule sufficiently taut so as to facilitate compression and flattening of the tubule;

(c) amplifying said target nucleic acid in said reaction vessel containing said mixture by PCR using a nucleic acid polymerase having 5' to 3' nuclease activity such that during an extension step of each PCR cycle, the nuclease activity of the nucleic acid polymerase allows cleavage and separation of the tag portion from the first quencher moiety on the annealing portion of the probe, said PCR being performed by cycling said mixture between two adjacent segments, held at different temperatures, of said reaction vessel;

(d) measuring a temperature-corrected signal from said reporter moiety on said oligonucleotide probe in said mixture while in one of the two adjacent segments, said mixture being at a first temperature at which the quenching oligonucleotide is bound to the tag portion;

(e) after a predetermined time interval, measuring a suppressed signal from the reporter moiety on said oligonucleotide probe in said mixture while in said one of the two adjacent segments, said mixture being at a second temperature within the same of said one of the two adjacent segments at which the quenching oligonucleotide is bound to the tag portion;

(f) obtaining a calculated signal value by subtracting the suppressed signal detected at the second temperature from the temperature-corrected signal detected at the first temperature;

(g) repeating steps (c) through (g) through multiple PCR cycles; and (h) measuring the calculated signal values from the multiple PCR cycles to detect the presence of the target nucleic acid.

2. The method of claim 1, wherein the tag portion comprises a modification such that it is not capable of being extended by the nucleic acid polymerase.

3. The method of claim 1, wherein the tag portion of the oligonucleotide probe, or the quenching molecule, or both the tag portion and the quenching molecule contain one or more nucleotide modifications.

4. The method of claim 3, wherein the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations thereof.

5. The method of claim 1, wherein the reporter moiety is a fluorescent dye and the quencher moiety is effective to quench a detectable signal from said fluorescent dye.

6. The method of claim 1, wherein the tag portion is attached to the 5' terminus of the annealing portion or to the 3' terminus of the annealing portion.

7. The method of claim 1, wherein the quenching oligonucleotide is connected to the tag portion of the second oligonucleotide probe via a stem-loop structure.

8. A reaction vessel, comprising:
(a) a proximal end having an opening through which a sample is introducible;
(b) a distal end; and
(c) at least a first segment containing at least one nucleic acid extraction reagent, a second segment distal to the first segment and containing a wash reagent, and a third segment distal to the second segment and containing one or more amplification reagents, each of said segments being:
   (i) defined by the tubule;
   (ii) fluidly isolated, at least in part, by a fluid-tight seal formed by a bonding of opposed wall portions of the tubule to one another such that:
      (A) the seal is broken by application of fluid pressure on a segment that is fluidly isolated in part by the seal; and
      (B) the seal is capable of being clamped where the opposed wall portions of the tubule are bonded, without breaking the seal, to prevent the seal from being broken by application of fluid pressure on a segment that is fluidly isolated in part by the seal;
   (iii) so expandable as to receive a volume of fluid expelled from another segment; and so compressible as to contain substantially no fluid when so compressed;
(d) a cap for closing the opening, the cap containing a chamber in fluid communication with the tubule, and the cap permitting free escape of gasses but retaining all liquid volumes and infectious agents in the tube;
(e) a rigid frame to which the tubule's proximal and distal ends are held; and
(f) an integral tubule tensioning mechanism or an attachment of the tubule to the frame that pulls the tubule sufficiently taut so as to facilitate compression and flattening of the tubule;
(g) said reaction vessel containing:
   (i) at least one pair of oligonucleotide primers, each oligonucleotide primer of said pair being capable of hybridizing to opposing strands of a subsequence of said target nucleic acid;
   (ii) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of said target nucleic acid that is bounded by said pair of oligonucleotide primers, said probe further comprising an interactive dual label comprising a reporter moiety located on said tag portion and a first quencher moiety located on said annealing portion, and wherein said reporter moiety is separated from said first quencher moiety by a nuclease susceptible cleavage site; and wherein said tag portion hybridizes to a quenching oligonucleotide that comprises one or more quencher moieties capable of quenching said reporter moiety when said quenching oligonucleotide is hybridized to said tag portion.

9. The reaction vessel of claim 8, further comprising a filter, structured so as to separate selected components of a sample material from other components of the sample material.

10. The reaction vessel of claim 8, wherein the nucleic acid extraction reagent is a cell lysis reagent.

11. The reaction vessel of claim 8, wherein the mixture further comprises at least one member of the group consisting of: a nucleotide, an enzyme, a DNA polymerase, a template DNA, an oligonucleotide, a primer, a dye, a marker, a molecular probe, a buffer, and a detection material.

12. The reaction vessel of claim 8, wherein the reaction vessel includes a self-sealing injection channel formed therein, the self-sealing injection channel being capable of fluid communication with the sample material in the sample-containing vessel.

13. The reaction vessel of claim 8, wherein the cover comprises a reservoir.

14. The reaction vessel of claim 8, further comprising a sampling instrument attached to the cover.

15. The reaction vessel of claim 14, wherein the sampling instrument is selected from one of a pipette, a needle, a stick, and a tweezer.

16. The reaction vessel of claim 8, wherein the segments form a substantially linear array.

17. The reaction vessel of claim 8, wherein the segments form a contiguous array.

18. The reaction vessel of claim 8, wherein at least one fluid-tight seal extends substantially across the entire width of the reaction vessel.

19. A sample processing apparatus, comprising:
  (a) a processing unit having an opening to receive a sample vessel containing a sample, the processing unit having a first processing station, a second processing station, and a third processing station positional along the opening,
  (b) the first processing station including a first compression member adapted to compress the sample vessel within the opening and a first energy transfer element for transferring energy to the sample at the first processing station,
  (c) the second processing station including a second compression member adapted to compress the sample vessel within the opening and a second energy transfer element for transferring energy to the sample at the second processing station, and
  (d) the third processing station including a third compression member adapted to compress the sample vessel within the opening and a third energy transfer element for transferring energy to the sample at the third processing station,
  wherein compression of the sample vessel by one of the compression members displaces the sample within the sample vessel between the processing stations; and
  (e) a reaction vessel insertable in said opening and comprising
    (i) a proximal end having an opening through which a sample is introducible;
    (ii) a distal end; and
    (iii) at least a first segment containing at least one nucleic acid extraction reagent, a second segment distal to the first segment and containing a wash reagent, and a third segment distal to the second segment and containing one or more amplification reagents, each of said segments being:
      (A) defined by the tubule;
      (B) fluidly isolated, at least in part, by a fluid-tight seal formed by a bonding of opposed wall portions of the tubule to one another such that:
        (a) the seal is broken by application of fluid pressure on a segment that is fluidly isolated in part by the seal; and
        (b) the seal is capable of being clamped where the opposed wall portions of the tubule are bonded, without breaking the seal, to prevent the seal from being broken by application of fluid pressure on a segment that is fluidly isolated in part by the seal;
      (C) so expandable as to receive a volume of fluid expelled from another segment; and so compressible as to contain substantially no fluid when so compressed;
  (iv) a cap for closing the opening, the cap containing a chamber in fluid communication with the tubule, and the cap permitting free escape of gasses but retaining all liquid volumes and infectious agents in the tube;
  (v) a rigid frame to which the tubule's proximal and distal ends are held; and
  (vi) an integral tubule tensioning mechanism or an attachment of the tubule to the frame that pulls the tubule sufficiently taut so as to facilitate compression and flattening of the tubule;
  (vii) one of said segments containing:
    (A) at least one pair of oligonucleotide primers, each oligonucleotide primer of said pair being capable of hybridizing to opposing strands of a subsequence of said target nucleic acid;
    (B) an oligonucleotide probe, comprising a tag portion and an annealing portion on the same strand, wherein the tag portion comprises a nucleotide sequence non-complementary to the target nucleic acid sequence, and the annealing portion comprises a nucleotide sequence at least partially complementary to the target nucleic acid sequence and which hybridizes to a region of said target nucleic acid that is bounded by said pair of oligonucleotide primers, said probe further comprising an interactive dual label comprising a reporter moiety located on said tag portion and a first quencher moiety located on said annealing portion, and wherein said reporter moiety is separated from said first quencher moiety by a nuclease susceptible cleavage site; and wherein said tag portion hybridizes to a quenching oligonucleotide that comprises one or more quencher moieties capable of quenching said reporter moiety when said quenching oligonucleotide is hybridized to said tag portion.

* * * * *